(12) United States Patent
Pereira et al.

(10) Patent No.: US 9,980,746 B2
(45) Date of Patent: May 29, 2018

(54) LOCKING MEMBER FOR A MEDICAL ASSEMBLY DELIVERY DEVICE

(71) Applicant: Boston Scientific Scimed, Inc., Maple Grove, MN (US)

(72) Inventors: Peter J. Pereira, Mendon, MA (US); Sharmad S. Joshi, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 362 days.

(21) Appl. No.: 14/724,069

(22) Filed: May 28, 2015

(65) Prior Publication Data

US 2015/0342637 A1 Dec. 3, 2015

Related U.S. Application Data

(60) Provisional application No. 62/004,531, filed on May 29, 2014.

(51) Int. Cl.
| | |
|---|---|
| *A61B 17/34* | (2006.01) |
| *A61B 17/06* | (2006.01) |
| *A61F 2/00* | (2006.01) |
| *A61B 17/00* | (2006.01) |

(52) U.S. Cl.
CPC .... *A61B 17/3468* (2013.01); *A61B 17/06109* (2013.01); *A61B 2017/00805* (2013.01); *A61F 2/0045* (2013.01); *A61F 2220/0033* (2013.01)

(58) Field of Classification Search
CPC .......... A61B 17/3468; A61B 17/06109; A61B 2017/00805; A61F 2/0045; A61F 2220/0033; E05B 15/0086; E05B 81/28; E05B 41/00; Y10S 292/38; Y10T 16/529

USPC ................ 292/4, 41, 137, 166–170, 307, 80
See application file for complete search history.

(56) References Cited

U.S. PATENT DOCUMENTS

| | | | | |
|---|---|---|---|---|
| 8,602,965 | B2 | 12/2013 | Chu et al. | |
| 2002/0099259 | A1* | 7/2002 | Anderson | .......... A61B 17/0482 600/29 |
| 2006/0283217 | A1* | 12/2006 | Ramsauer | ................. E05C 1/16 70/162 |
| 2010/0094079 | A1* | 4/2010 | Inman | ................ A61B 17/0401 600/30 |
| 2010/0274074 | A1* | 10/2010 | Khamis | ............ A61B 17/00234 600/37 |

(Continued)

*Primary Examiner* — Christine H Matthews
*Assistant Examiner* — Kaylee Wilson
(74) *Attorney, Agent, or Firm* — Brake Hughes Bellermann LLP

(57) ABSTRACT

A medical assembly and method for the delivery of an implant inside a patient's body. The medical assembly includes an implant, a tubular member, and a delivery device. The tubular member includes a proximal portion defining a first locking feature. The delivery device includes a needle having a proximal portion and a handle having a proximal portion and a distal portion coupled to the proximal portion of the needle. The distal portion of the handle also includes a locking member that defines an opening, the opening being configured to allow at least a portion of the tubular member to pass through the locking member when the locking member is in an unlocked configuration and the locking member configured to engage the first locking feature of the tubular member to prevent the tubular member from being removed from the locking member when the locking member is in a locked configuration.

20 Claims, 20 Drawing Sheets

(56) References Cited

U.S. PATENT DOCUMENTS

2011/0230703 A1 9/2011 Young et al.
2014/0257025 A1* 9/2014 Chu .................... A61F 2/0045
600/30

* cited by examiner

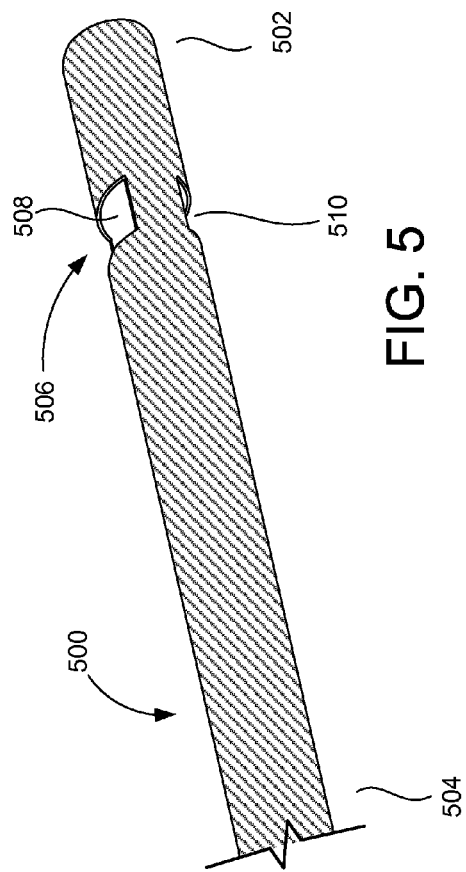
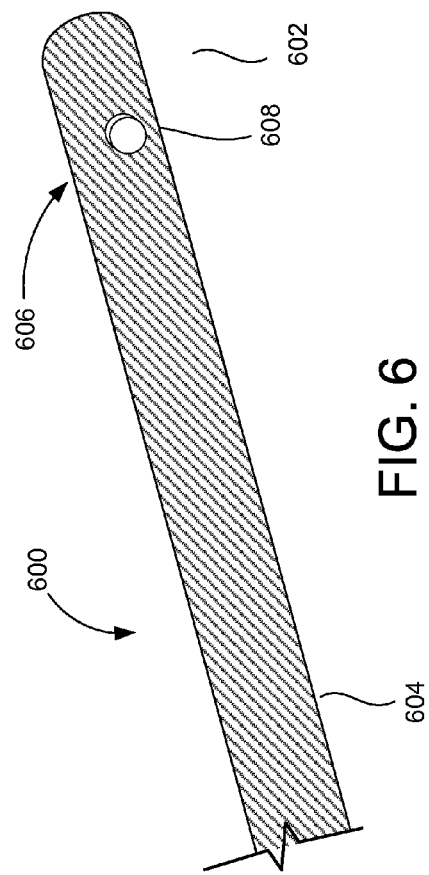

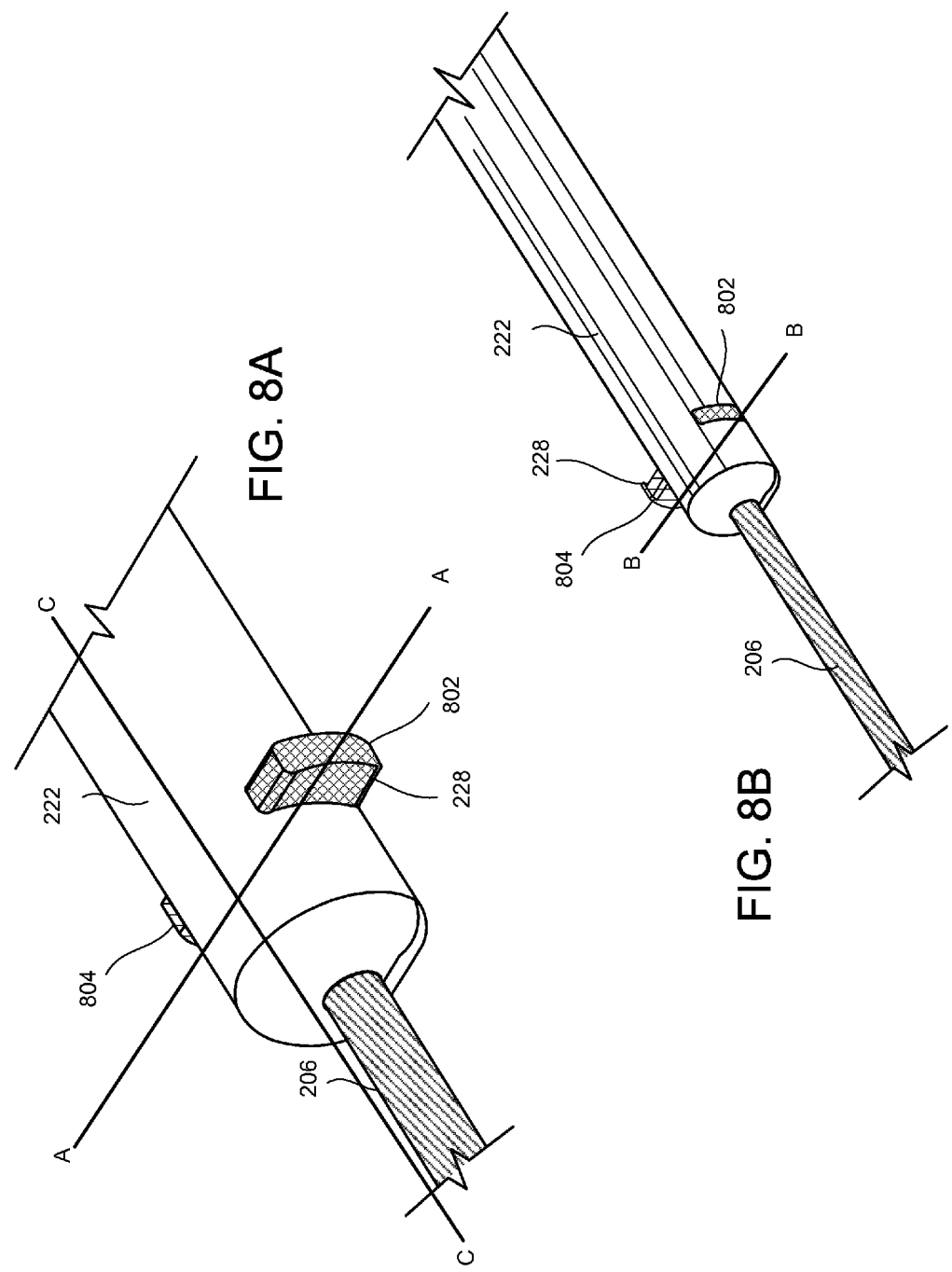

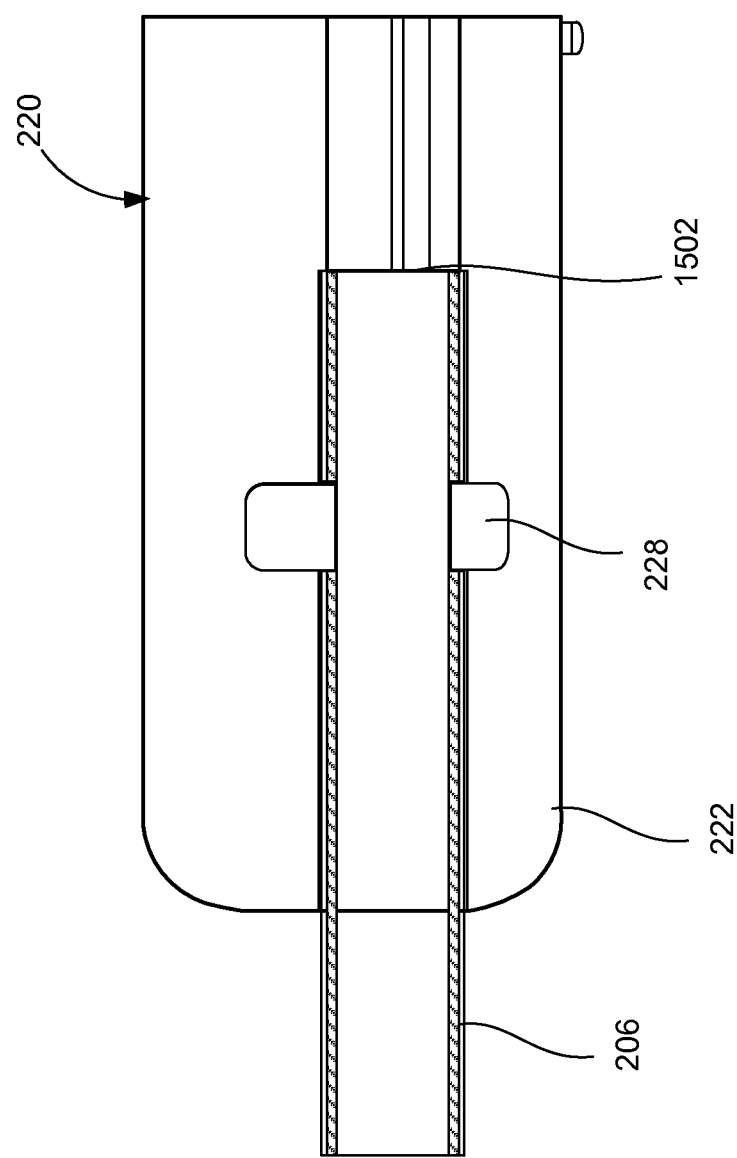

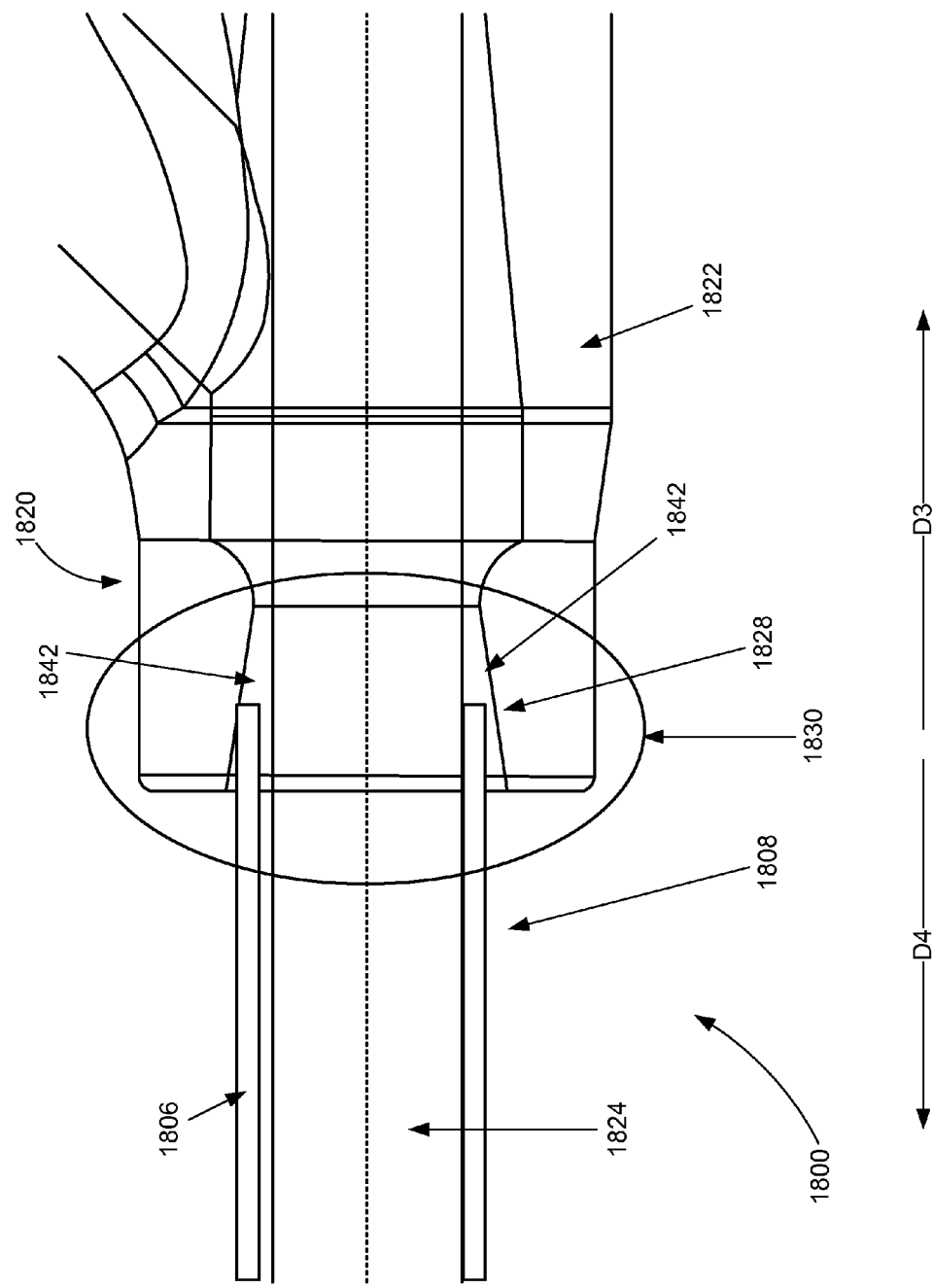

LOCKING MEMBER FOR A MEDICAL ASSEMBLY DELIVERY DEVICE

CROSS-REFERENCE TO RELATED APPLICATION

This application is a Nonprovisional of, and claims priority to, U.S. Patent Application No. 62/004,531, filed on May 29, 2014, entitled "LOCKING MEMBER FOR A MEDICAL ASSEMBLY DELIVERY DEVICE", which is incorporated by reference herein in its entirety.

TECHNICAL FIELD

The present disclosure generally relates to surgical devices and procedures, particularly devices and methods for the delivery of implants within a patient's body.

BACKGROUND

Anatomical tissues such as pelvic tissues may be weakened or damaged with age, injury, or disease. This decrease in structural integrity of anatomical tissues may have significant medical consequences, which in turn might influence the biological functions of the tissues. There are various surgical procedures for treating such dysfunction of the tissues. For example, implants can be placed into a patient to provide support for the weakened or damaged tissue. The support provided by the implant replicates the natural position and structure of the tissue, and thereby helps in decreasing or eliminating impairment of biological functions resulting from tissue weakening or damage.

These surgical procedures may use a delivery device to deliver the implant at the anatomical tissue inside the patient's body. Such a delivery device assists in the delivery and placement of the implant. The delivery device may include a needle coupled with the implant, for example through a tubular member of the implant, such as a dilator. When the delivery device is coupled with the tubular member, the tubular member passes through tissues that have already been pierced by the needle, thereby dilating a needle track for ease of the implant introduction and positioning within the patient. However, if the delivery device releases from the tubular member inadvertently the surgeon or other operator may need to re-couple the implant to the delivery device, adding time and frustration to the procedure.

In view of the above, there may be a need for a delivery device and a surgical procedure that facilitates in keeping the tubular member intact with the delivery device during introduction into a patient, thereby helping to prevent premature and inadvertent release of the tubular member.

SUMMARY

The present disclosure provides delivery devices with a locking mechanism that prevents inadvertent or premature release of an implant from the delivery device. The present disclosure also provides methods for manufacturing and using the disclosed delivery devices.

One illustrative embodiment discloses a delivery device having a handle having a proximal portion and a distal portion, wherein the distal portion of the handle is coupled to a proximal portion of a needle and the distal portion of the handle is configured to accept a proximal portion of a tubular member of a medical device assembly. The distal portion of the handle includes a locking member, the locking member being configured to be placed in a locked configuration and an unlocked configuration, the locking member having a first end and a second end and defining an opening. The opening may be configured to allow a proximal portion of the tubular member to pass through the locking member when the locking member is in the unlocked configuration and configured to prevent the tubular member from being removed from the locking member when the locking member is in the locked configuration. When in the locked configuration, the locking member ensures the tubular member stays intact with the delivery device, preventing premature or inadvertent release of the tubular member. The first end of the locking member may protrude from a first side of the handle when the locking member is in the unlocked configuration and the second end may protrude from a second side of the handle when the locking member is in the locked configuration. In addition, the first end of the locking member may have a first visual appearance and the second end may have a second visual appearance that enables an operator of the delivery device to ensure that the locking member is in an unlocked or locked configuration, respectively. The first visual appearance may be one color, for example green and the second visual appearance may be another color, for example red. In addition or alternatively, the first visual appearance may include a first image and the second visual appearance may include a second image.

In addition or alternatively, the locking member may be configured to slide from the unlocked configuration to the locked configuration in response to pressure on the first end and configured to slide from the locked configuration to the unlocked configuration in response to pressure on the second end.

In some embodiments, the locking member includes a protrusion proximate the first end, the protrusion configured to couple with a first locking feature of the tubular member when the locking member is in the locked configuration. In addition or alternatively, the locking member may also include a protrusion proximate the first end configured to imbed at least partially into the tubular member when the locking member is in the locked configuration. In addition or alternatively, the locking member includes a first protrusion proximate the first end, the first protrusion configured to slide into an aperture defined by the tubular member when the locking member is moved from the unlocked configuration to the locked configuration. In addition or alternatively, the opening includes a narrower portion proximate the first end of the locking member and a wider portion proximate the second end of the locking member, the narrower portion configured to prevent, via a friction fit, the tubular member from being removed and the wider portion configured to permit free axial movement of the tubular member.

Another illustrative embodiment discloses a medical assembly that includes an implant for placement in a body of a patient, a tubular member configured to be coupled to the implant and including a proximal portion and a distal portion, the proximal portion defining a first locking feature, and a delivery device configured to deliver the implant. The delivery device includes a needle having a proximal portion and a distal portion such that the tubular member is positioned over the needle, and a handle having a proximal portion and a distal portion, wherein the distal portion of the handle is coupled to the proximal portion of the needle and the distal portion of the handle is configured to accept the proximal portion of the tubular member. The delivery device also includes a locking member in the distal portion of the handle, the locking member being configured to be placed in a locked configuration and an unlocked configuration, the locking member defining an opening, the opening being configured to allow at least a portion of the tubular member to pass through the locking member when the locking member is in the unlocked configuration and the locking member configured to engage the first locking feature of the tubular member to prevent the tubular member from being removed from the locking member when the locking member is in the locked configuration.

In addition, the locking member may have a first end that protrudes from a first side of the handle when the locking member is in the unlocked configuration and a second end that protrudes from a second side of the handle when the locking member is in the locked configuration. In addition, the first end may have a first visual appearance and the second end may have a second visual appearance that differs from the first visual appearance. In addition or alternatively, the first visual appearance can be green and the second visual appearance can be red.

In addition or alternatively, the first locking feature may be an aperture and the locking member can further include a protrusion configured to couple with the first locking feature of the tubular member when the locking member is in the locked configuration. In addition or alternatively, the first locking feature may be an aperture and the locking member may further include a protrusion configured to slide into the first locking feature of the tubular member when the locking member is in the locked configuration. In addition or alternatively, the first locking feature may be a penetrable material and the locking member may further include a protrusion configured to imbed into the penetrable material when the locking member is in the locked configuration. In addition or alternatively, the opening may include a narrower portion proximate a first end of the locking member and a wider portion proximate a second end of the locking member, the narrower portion configured to prevent the locking member from moving from the locked configuration to the unlocked configuration absent pressure applied to the second end of the locking member.

Another illustrative embodiment discloses a method for treatment of a pelvic floor disorder in a patient's body. The method includes ensuring a locking member of a delivery device is in an unlocked configuration, the locking member being in a distal end of a handle of the delivery device and the unlocked configuration indicated by a first end of the locking member protruding from a first side of the handle and a second end of the locking member opposite the first end being substantially flush with a second side of the handle. The method also includes inserting a tubular member of a medical device assembly over a needle of the delivery device and through an opening defined by the locking member, the medical device assembly including an implant and moving the locking member from the unlocked configuration to a locked configuration, the locked configuration preventing the tubular member from being removed from the locking member, the locked configuration indicated by the second end protruding from the second side of the handle and the first end being substantially flush with the first side of the handle. The method also includes inserting the delivery device and the tubular member inside the patient's body, disassociating the tubular member from the delivery device once the delivery device reaches a target body location in a pelvic floor region by placing the locking member into the unlocked configuration, and fixing the implant at a first location within the pelvic floor region.

In some implementations, the first end of the locking member has a first visual appearance and the second end of the locking member has a second visual appearance, the first visual appearance assisting in ensuring that the locking member is in the unlocked configuration and the second visual appearance assisting in ensuring that the locking member is in the locked configuration. In addition or alternatively, the method may include aligning a protrusion of the locking member with a first locking feature of the tubular member prior to ensuring the locking member is moved from the unlocked configuration to the locked configuration.

BRIEF DESCRIPTION OF THE FIGURES

The disclosure may be more completely understood in consideration of the following detailed description of various embodiments in connection with the accompanying drawings.

FIG. 5 illustrates an enlarged and isolated partial prospective view of a tubular member of a medical device assembly, according to one embodiment.

FIG. 6 illustrates an enlarged and isolated partial prospective view of a tubular member of a medical device assembly, according to another embodiment.

FIG. 8A illustrates an enlarged and isolated partial perspective view of the medical assembly of FIG. 2 in an unlocked configuration, according to an embodiment.

FIG. 8B illustrates an enlarged and isolated partial perspective view of the medical assembly of FIG. 2 in a locked configuration, according to an embodiment.

FIG. 15 illustrates a cross-section view of the medical assembly of FIG. 8A along line C-C, according to an embodiment.

FIG. 18 illustrates a side view of an inner-profile of a medical assembly, according to an embodiment.

DETAILED DESCRIPTION

Definitions of certain terms are provided below and shall be applied, unless a different definition is given in the claims or elsewhere in this specification.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings, in which similar elements in different drawings are identified with the similar reference numbers. The drawings, which are not necessarily to scale, depict illustrative embodiments and are not intended to limit the scope of the disclosure.

The devices and methods described herein are generally directed to implants and the delivery and placement of such implants within a pelvic region of a patient. In other embodiments, the devices and methods may be used to place implants in other locations within the body of the patient.

The terms proximal and distal described in relation to various medical devices and their components are referred with a point of reference. The point of reference, as used in this description, is a perspective of an operator. The operator may be a surgeon, a physician, a nurse, a doctor, a technician, and the like, who may perform the procedure of surgery through the patient's body orifice as described herein. The term proximal refers to an area that is closest to the operator. The term distal refers to an area that is farthest from the operator. The patient referred here can be a human female, male, or any other animal.

Figure 1:
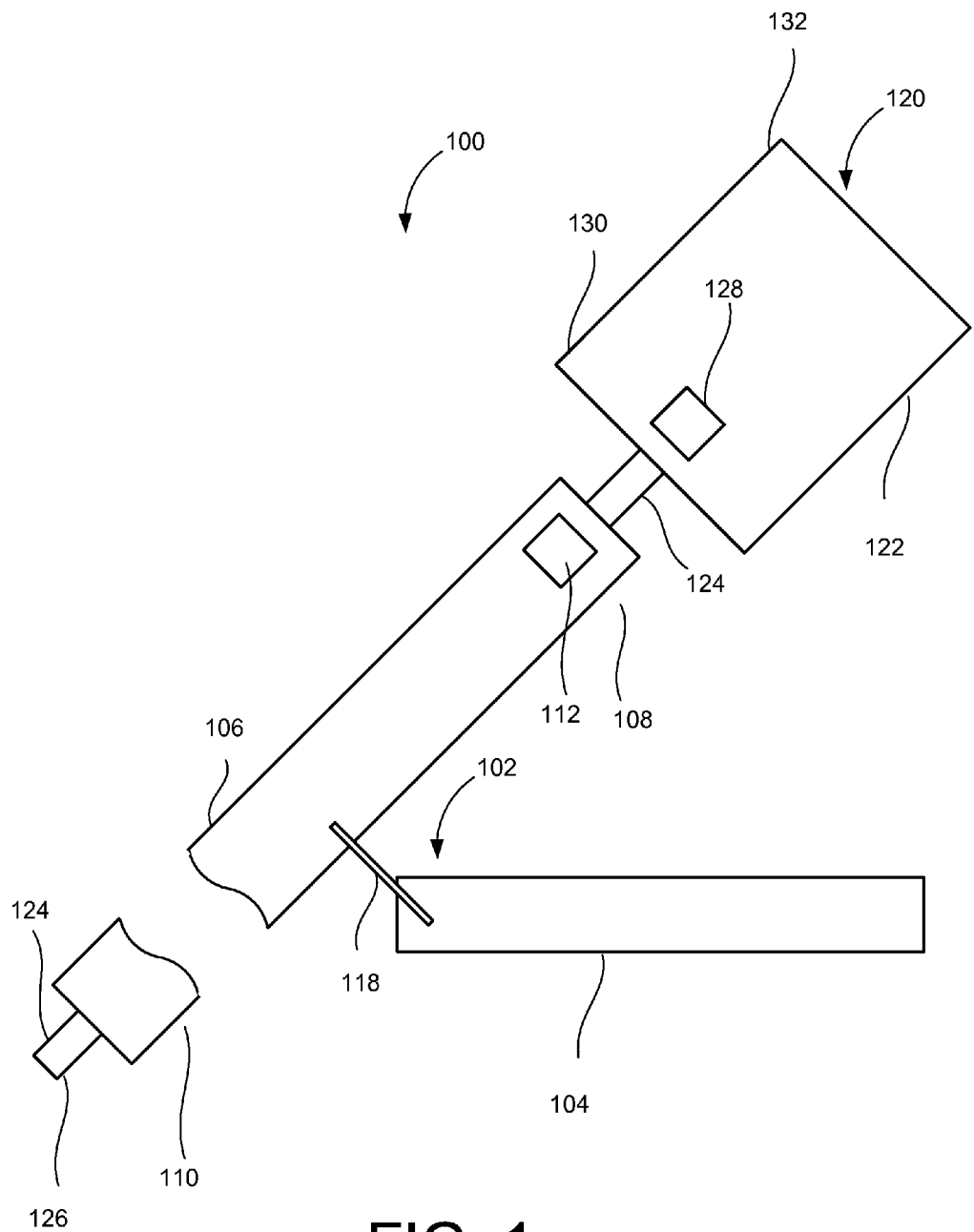
FIG. 1 illustrates a schematic diagram of a medical assembly, according to an embodiment.

FIG. 1 is a schematic view of a medical assembly 100 according to an embodiment. The medical assembly 100 includes a medical device assembly 102, such as a sling assembly used to treat a pelvic floor disorder. The medical device assembly 102 can be, for example, a retropubic incontinence sling configured to be delivered by way of a transvaginal approach or a transobturator approach or vaginal pre-pubic approach or can be delivered through other approaches and positioned at various locations within a patient's body. The medical device assembly 102 includes an implant 104 and a tubular member 106 that defines a lumen. The tubular member 106 can include a proximal portion 108 and a distal portion 110. The tubular member 106 can be configured to be coupled to the implant 104. For example, the tubular member 106 may be coupled to the implant 104 using a sleeve member 118. The tubular member 106 can be configured to expand an opening in a patient's body allowing insertion of the implant 104 and a delivery device 120 as they follow the tubular member 106 into the opening within a patient's body. In an embodiment, the tubular member 106 can be made from one or more biocompatible materials such as a plastic or metal. In an example, the tubular member 106 can be made of a semi-rigid plastic material. Examples of such materials include, but are not limited to, polyethylene terephthalate (PET), polyethylene (PE), or ethylene vinyl acetate (EVA). In some embodiments, the tubular member 106, or a portion of the tubular member 106 at a proximal end, may be made of flexible, penetrable material, such as silicone, polyurethane, PEBAX, low density polyethylene, felt, TEFLON, thermoplastic elastomers, etc. In some embodiments, the cross section of the tubular member 106 can be circular, substantially flat or triangular in shape or can be of any other shape. In other embodiments, the cross section of the tubular member 106 can be substantially rectangular and tapered at the distal portion 110. In embodiments, the tubular member 106 can be employed of any shape as per the requirements in a specific surgical procedure. In an embodiment, the tubular member 106 defines a hollow passageway, or lumen, along a length of the tubular member 106 extending between the distal portion 110 to the proximal portion 108 of the tubular member 106. In an embodiment, the tubular member 106 is a first tubular member that can be attached to a first end portion of the implant 104 and the medical device assembly 102 also includes a second tubular member similar to the tubular member 106 that can be attached to a second end portion of the implant 104.

The proximal portion 108 of the tubular member 106 may include a first locking feature 112. In an embodiment, the first locking feature 112 includes a recessed area. The recessed area may be an aperture or a recess or cavity in the sidewall of the tubular member 106. The recessed area can be formed of various shapes and sizes. Exemplary shapes can be a rectangle, a square, an oval, or a round shape. In another embodiment, the first locking feature 112 includes an area of penetrable material. For example, an area of tubular member 106 may be made of the penetrable material or the entire tubular member 106 may be made of the penetrable material. Such material may allow a protrusion, e.g., a spike or barb, in a locking member of a delivery device to imbed into the tubular member 106. In certain embodiments, the tubular member 106 lacks the first locking feature 112. The implant 104 may be coupled to the tubular member 106 via sleeve member 118.

The medical assembly 100 also includes a delivery device 120. The delivery device 120 can be configured to deliver the medical device assembly 102 to a target location inside the body of a patient. The delivery device 120 can include a needle 124. The diameter and length and curvature of the needle 124 can depend on surgical requirements. In certain embodiments, the delivery device 120 can be designed so as to be adapted to be used in a trans-vaginal retro pubic approach. In certain embodiments, the needle 124 can be a surgical needle with a substantially small outer diameter for minimally invasive surgery. In some embodiments, the needle diameter may be 2 mm to 10 mm.

The needle 124 has a proximal portion and a distal portion. The needle 124 may include a tip portion 126 at its distal portion. In some embodiments, the tip portion 126 may be sharp and configured to pierce or dissect tissue layers and create a passageway within bodily tissues to deliver and place the implant 104 inside the patient's body. In some embodiments, the needle 124 can be made of stainless steel or other medical grade metal.

In some embodiments, the needle 124 may be configured to be removably positioned within the lumen defined by the tubular member 106. In an embodiment, the tubular member 106 can be positioned over the needle 124 by sliding the tubular member 106 over the needle 124, thereby forming a removable connection between the two. In some embodiments, the tubular member is formed of a flexible material and the tubular member 106 can be sized to assume the shape of the needle 124 on its insertion within the lumen.

The delivery device 120 further includes a handle 122. In some embodiments, the handle 122 is made up of a plastic material or suitable metals, for example aluminum or stainless steel. Exemplary plastic materials include polycarbonate, lexan, Acrylonitrile butadiene styrene (ABS), and the like without limitations. In an embodiment, the handle 122 has a proximal portion 132 and a distal portion 130 such that the distal portion 130 of the handle 122 can be fixably coupled to the proximal portion of the needle 124. In other words, the handle 122 and the needle 124 are not separable during normal operation of the delivery device 120. In an embodiment, the distal portion 130 of the handle 122 can include a second locking feature 128. The second locking feature 128 can be configured to releasably couple with the first locking feature 112. For example, the second locking feature 128 may include a locking member having a protrusion configured to couple with or slide into the first locking feature 112 of the tubular member 106. In another embodiment, the second locking feature 128 includes a protrusion configured to imbed at least partially into the tubular member 106. In some embodiments, the second locking feature 128 may be a friction lock that is configured to frictionally couple the tubular member 106 to the handle 122. In one embodiment, the second locking feature 128 may frictionally couple the tubular member 106 after the tubular member 106 passes through an opening defined by the second locking feature 128. The second locking feature 128 may be placed into a locked configuration and into an unlocked configuration. In an embodiment, the second locking feature 128 may include a sliding member that is configured to slide from a locked configuration into an unlocked configuration and vice versa. When in the locked configuration, the second locking feature 128 may engage the tubular member 106, so that the tubular member 106 cannot be removed from the second locking feature 128.

In some embodiments, the second locking feature 128 may include a visual indication of whether the sliding mechanism is in the locked configuration or the unlocked configuration. For example, in the unlocked configuration a first end of the second locking feature 128 may protrude from the handle 122 of the delivery device 120 and the first end may have a first visual appearance. In one example, the first end may have a first color, for example appearing green. In another example, the first end may have an image, such as the words "unlocked" or a picture of an unlocked padlock, etc. imprinted on the first end. Imprinting includes engraving, etching, applying of ink or paint, etc. When the first end protrudes from the handle 122 the first visual appearance provides confirmation to an operator of the delivery device 120 that the second locking feature 128 is in the unlocked configuration. In the locked configuration a second end of the second locking feature 128 may protrude from the handle 122 of the delivery device 120 and the second end may have a second visual appearance. In one example the second end may appear a different color, for example red. In another example, the second end may include a second imprinted image, such as the words "locked" or a picture of a locked padlock, etc. When the second end protrudes from the handle 122, the second visual appearance provides confirmation to an operator of the delivery device that the second locking feature 128 is in the locked configuration.

Figure 2:
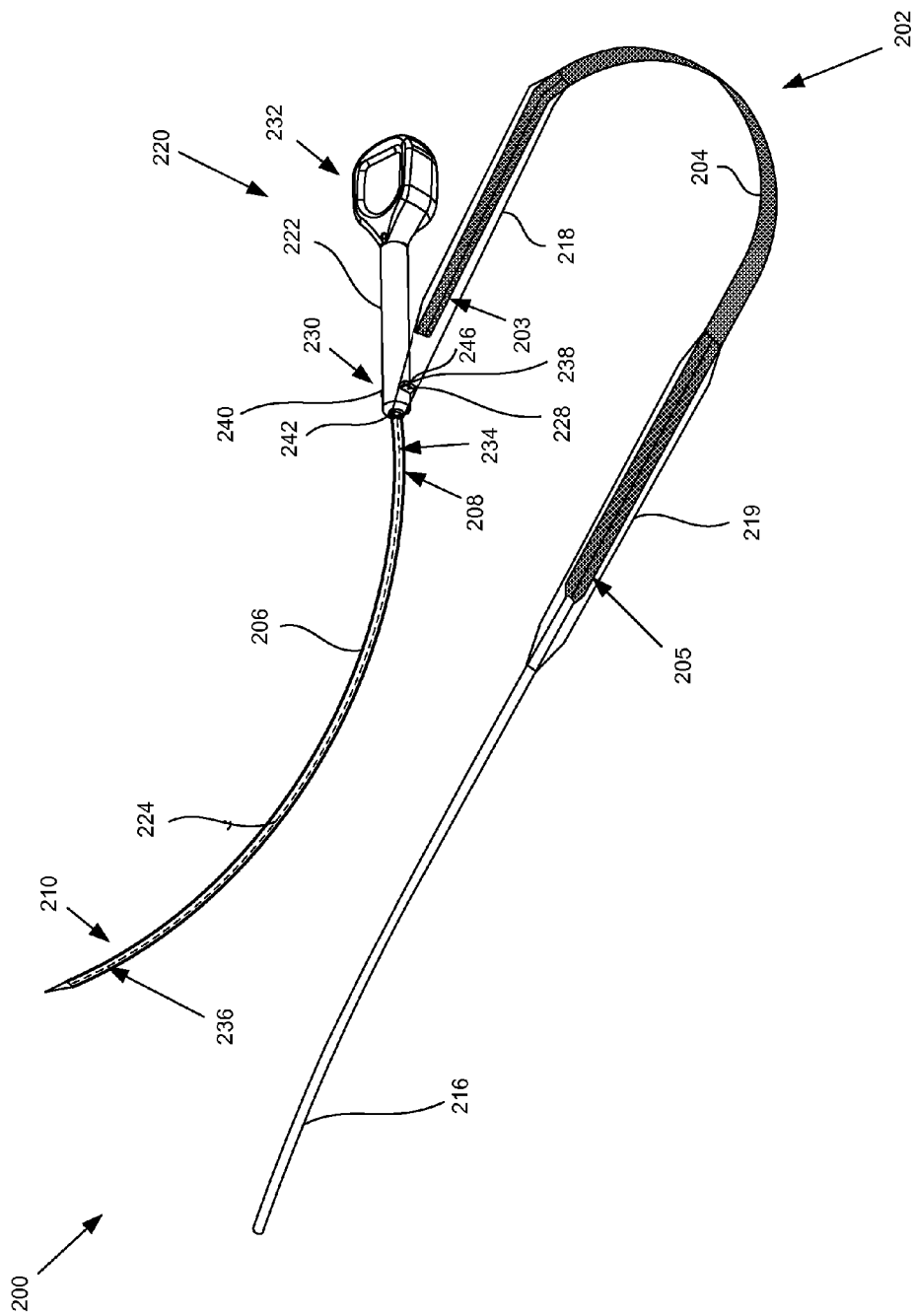
FIG. 2 illustrates a perspective view of a medical assembly, according to an embodiment.

FIG. 2 illustrates a perspective view of a medical assembly 200, according to an embodiment. The medical assembly 200 may include a delivery device 220 and a medical device assembly 202. The medical device assembly 202 may be an example of the medical device assembly 102 of FIG. 1. The medical device assembly 202 may include a first tubular member 206, an implant 204, and a first sleeve 218. In an example, the implant 204 of the medical device assembly 202 can be comprised of a polypropylene knitted mesh protected by or disposed within a disposable plastic sleeve, such as the first sleeve 218. At a first end portion 203 of the implant 204 is attached the first tubular member 206. The first tubular member 206 can be configured to facilitate passage of the implant 204 via delivery device 220 used to carry the implant 204 through bodily tissues for the transvaginal placement or through any other approach of placement. In some embodiments, the medical device assembly 202 may also include a second tubular member 216 and a second sleeve 219 at a second end 205 of the implant 204.

In accordance with various embodiments, the medical assembly 200 can include a delivery device 220 configured to deliver the medical device assembly 202. In an embodiment, the delivery device 220 can include a needle 224. In an embodiment, the needle 224 can be a surgical needle with a substantially small outer diameter for minimally invasive surgery. The needle 224 has a proximal portion 234 and a distal portion 236. In an embodiment, the first tubular member 206 can be positioned along a length of the needle 224. In an embodiment, the first tubular member 206 can include or define a lumen extending along the length of the tubular member 206 extending between the distal portion 210 and the proximal portion 208 of the first tubular member 206. The lumen allows the needle 224 to be inserted within the first tubular member 206. In some embodiments, the first tubular member 206 can be made of resilient or flexible material. In some embodiments, the material may be penetrable by a protrusion, for example a spike or barb. In an embodiment, the first tubular member 206 is open ended and tapered at the distal portion 210 to allow the needle 224 to protrude.

The first tubular member 206 can be coupled to the first sleeve 218 of the implant 204 through a suture. In an embodiment, a second tubular member 216, similar to the first tubular member 206, can be configured to be coupled at a second end portion 205 of the implant 204. In an embodiment, the second end portion 205 of the implant 204 can be protected by a second sleeve 219. The second tubular member 216 can be positioned along a length of a needle similar to the needle 224 described above.

The delivery device 220 further includes a handle 222 having a proximal portion 232 and a distal portion 230 and the needle 224 extends from the distal portion 230 of the handle 222. In an embodiment, the proximal portion 208 of the first tubular member 206 is configured to be received into the distal portion 230 of the handle 222, for example by a cavity 242 in the distal portion 230 of the handle 222. In an embodiment, the distal portion 230 of the handle 222 can include a locking member 228. The locking member 228 can be configured to releasably couple with a first locking feature of the first tubular member 206 or a similar first locking feature of the second tubular member 216. In an embodiment, the locking member 228 may include a sliding member 246 that has a length longer than a width of the handle 222, so that at least a portion of the sliding member 246 protrudes from the handle 222. The sliding member 246 may protrude from a first side 238 of the handle 222 when the locking member 228 is slid or otherwise moved with respect to the handle 222 to an unlocked configuration and from a second side 240 opposite the first side when the locking member 228 is moved to a locked configuration.

Figure 3A:
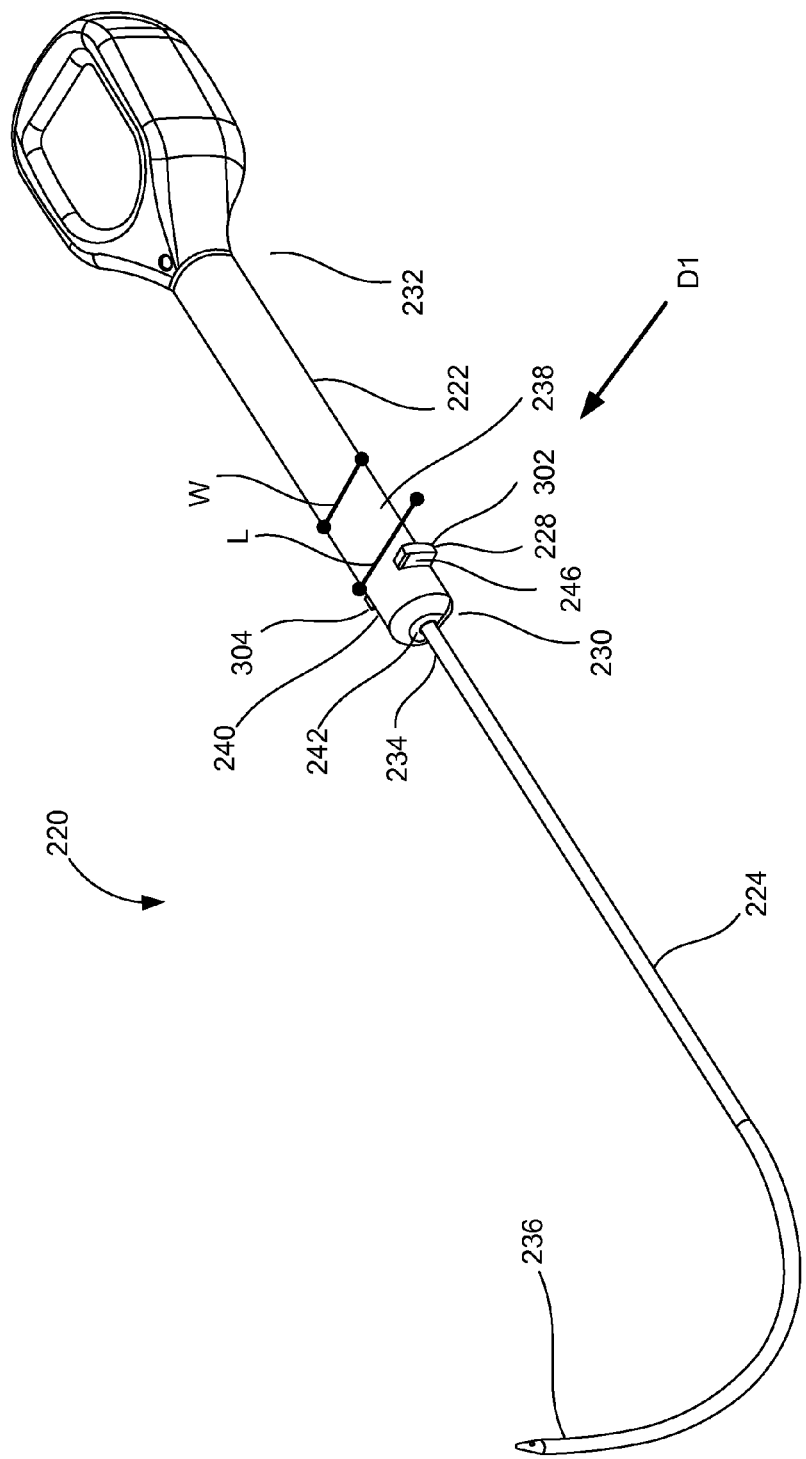
FIGS. 3A and 3B illustrate an example perspective view of a delivery tool for placing a medical device assembly within a body of a patient, in accordance with an embodiment.

FIG. 3A is an example perspective view of the delivery device 220 in an unlocked configuration, according to an embodiment. The delivery device 220 may be configured for placing a medical device assembly within a body of a patient. The delivery device 220 may include a handle 222, a needle 224, and a locking member 228. In an embodiment, the needle 224 can be a surgical needle with a substantially small outer diameter for minimally invasive surgery. The needle 224 has a proximal portion 234 and a distal portion 236. The needle 224 may be configured to be inserted into a tubular member of a medical assembly device, such as tubular member 206 of medical device assembly 202 of FIG. 2.

The delivery device 220 may also be configured to receive the proximal portion 208 of the tubular member 206 into a cavity 242 defined by the handle 222, for example at the distal portion 230 of the handle 222. The locking member 228 of the delivery device 220 may define an opening that allows a tubular member of a medical device assembly to pass through the locking member 228 when the locking member 228 is in an unlocked configuration.

In some embodiments, the locking member 228 may include a visual aid that allows an operator of the delivery device to quickly determine whether the delivery device 220 is in the locked configuration or the unlocked configuration. For example, the locking member 228 may have a length L longer than the width W of the handle 222. Thus, the locking member 228 may include a first end 302 that protrudes from the handle 222 when the locking member 228 is in the unlocked configuration. The first end 302 that protrudes from the handle 222 when the locking member 228 is in the unlocked configuration may have a first visual appearance. For example, the first end 302 may appear green or some other color that provides a signal to the operator that the tubular member is removable or, in other words, the tubular member may move axially along (e.g., along the length of) the needle 224 and possibly out of the handle 222. The locking member 228 may also include a second end 304 that is substantially flush with the handle 222 when the locking member 228 is in the unlocked configuration. Substantially flush means that the second end 304 may protrude a small amount from the handle 222, but by much less than the first end 302 when in the unlocked configuration.

Figure 3B:
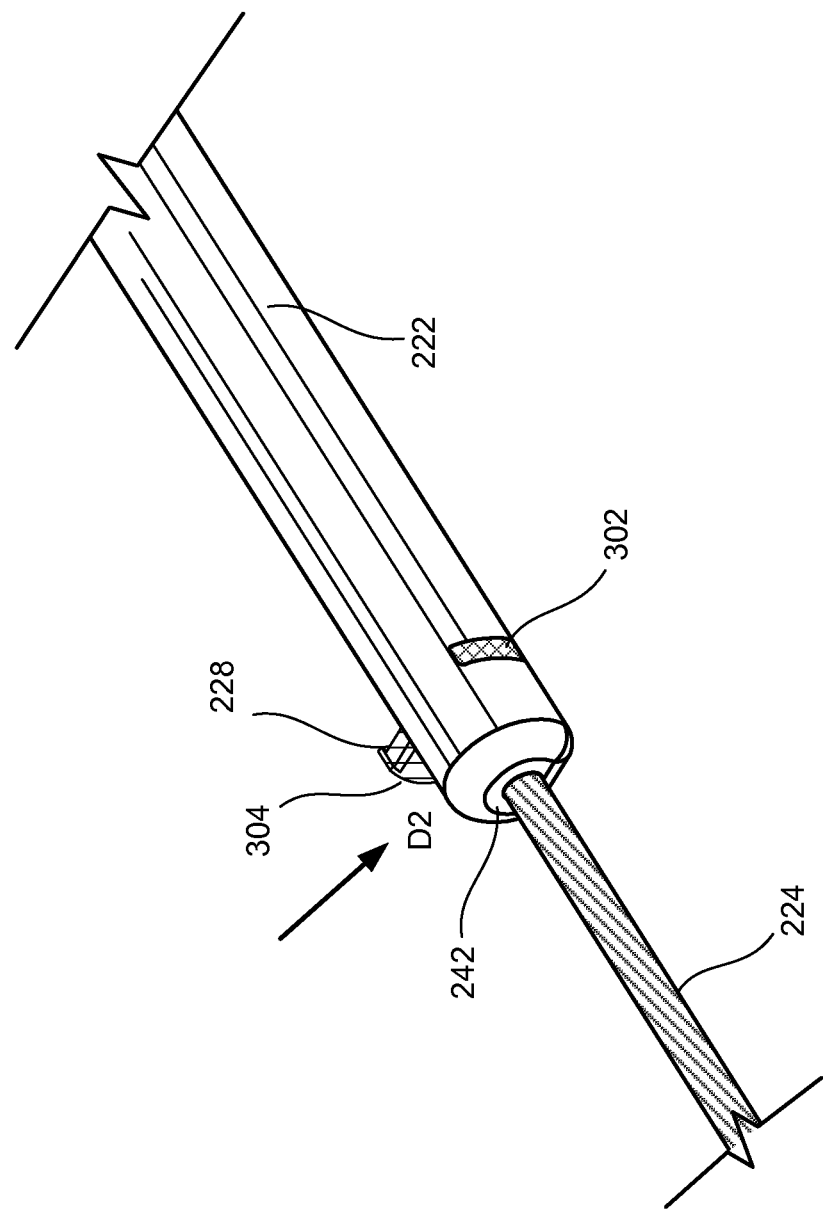

Conversely, when the locking member 228 is in a locked configuration the first end 302 may be substantially flush with the handle 222 and the second end 304 may protrude from the handle 222. The second end 304 may have a second visual appearance that differs from the first visual appearance of the first end 302. For example, the second end 304 may appear red, providing a visual indication that the locking member 228 is in the locked configuration. In the locked configuration, the locking member 228 may prevent the tubular member, when inserted into the handle 222 and through the opening defined by the locking member 228, from being removed from the handle 222. An operator may move the locking member 228 from the unlocked configuration to the locked configuration by pressing on the first end 302, causing the locking member 228 to slide in direction D1 of FIG. 3A until the first end 302 is substantially flush with the handle 222. This action results in the second end 304 protruding from the handle 222. FIG. 3B is a partial perspective view of the delivery device 220 of FIG. 3A in a locked configuration. FIG. 3B illustrates the second end 304 protruding from the handle 222 of the delivery device 220, and the first end 302 substantially flush with the handle 222. The operator may move the locking member 228 from the locked configuration to the unlocked configuration by pressing on the second end 304, causing the locking member 228 to slide in direction D2 of FIG. 3B until the second end 304 is substantially flush with the handle 222. This action results in the first end 302 protruding from the handle 222, as illustrated in FIG. 3A.

Figure 4:
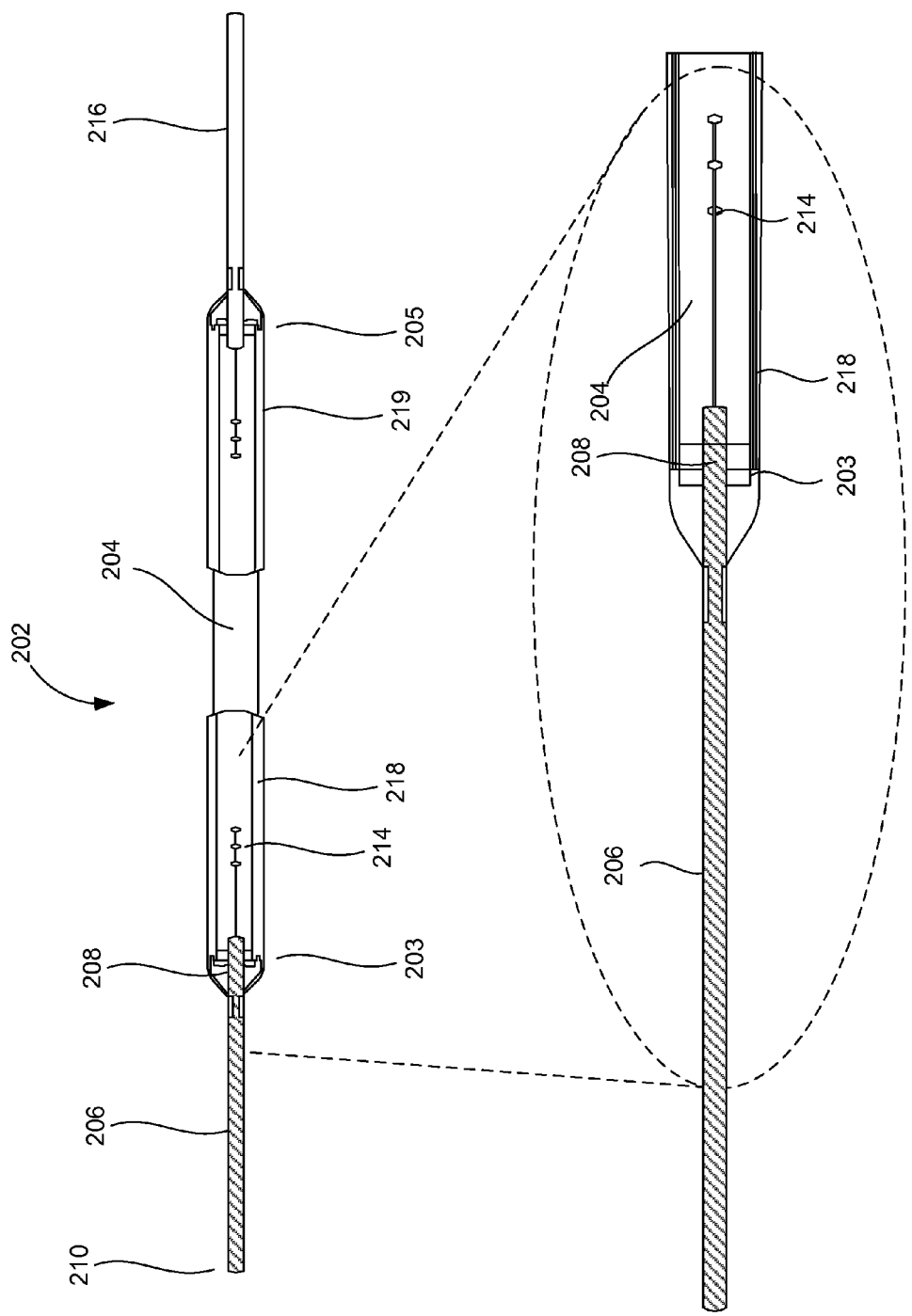
FIG. 4 illustrates a top view of an exemplary medical device assembly, according to an embodiment.

FIG. 4 is a perspective view of the example medical device assembly 202, in accordance with an embodiment of the invention. For ease of explanation and by way of example, the medical device assembly 202 is described as a sling assembly, although embodiments are not limited to sling assemblies and may include other types of medical device assemblies configured for delivery into the body of a patient. The sling assembly can be a retropubic incontinence sling configured to be delivered by way of a transvaginal approach or a transobturator approach or vaginal pre-pubic approach. In accordance with various embodiments, various sling assembly configurations can be possible. An exemplary sling assembly can include a first tubular member 206, an implant 204, and a first sleeve 218. In an example, the implant 204 of the sling assembly can be comprised of a polypropylene knitted mesh protected by disposable plastic sleeve such as the first sleeve 218. At a first end portion 203 of the implant 204 is attached the first tubular member 206. The first tubular member 206 can be configured to facilitate passage of the implant 204 via a delivery device used to carry the implant 204 through bodily tissues for the transvaginal placement or through any other approach of placement.

In an embodiment, the first tubular member 206 can be coupled to the implant 204 through a suture 214. In an exemplary embodiment, the suture 214 can form a first association loop to couple the first tubular member 206 with the implant 204. Various other coupling mechanisms or modes selected at least from the group consisting of glue, a staple, a fastener, or thread can be used to couple the tubular member 206 with the implant 204. In other embodiments, the implant 204 may be coupled to the first sleeve 218 and the first sleeve 218 may be coupled to the first tubular member 206. First sleeve 218 may extend along a partial length of implant 204. More than one sleeve 218 may be utilized, for example, a sleeve on each half of the implant. In an embodiment, the first sleeve 218 is wrapped around and attached to at least a portion of the tubular member 206. In an embodiment, the first tubular member 206 can include a proximal portion 208 and a distal portion 210. The proximal portion 208 of the first tubular member 206 can include a first locking feature. The first locking feature can be one of a number of locking features, as will be described in further detail with regard to FIGS. 5-7. In some embodiments, the medical assembly may include a second tubular member 216, a second sleeve 219, and a second suture at a second end portion 205 of the implant 204. In such embodiments, the second tubular member 216 may be configured like the first tubular member 206, for example having a similar locking feature at the proximal portion. Although described as having a locking feature, in some embodiments the locking feature on the tubular member 206 is optional and not needed.

Figure 7:
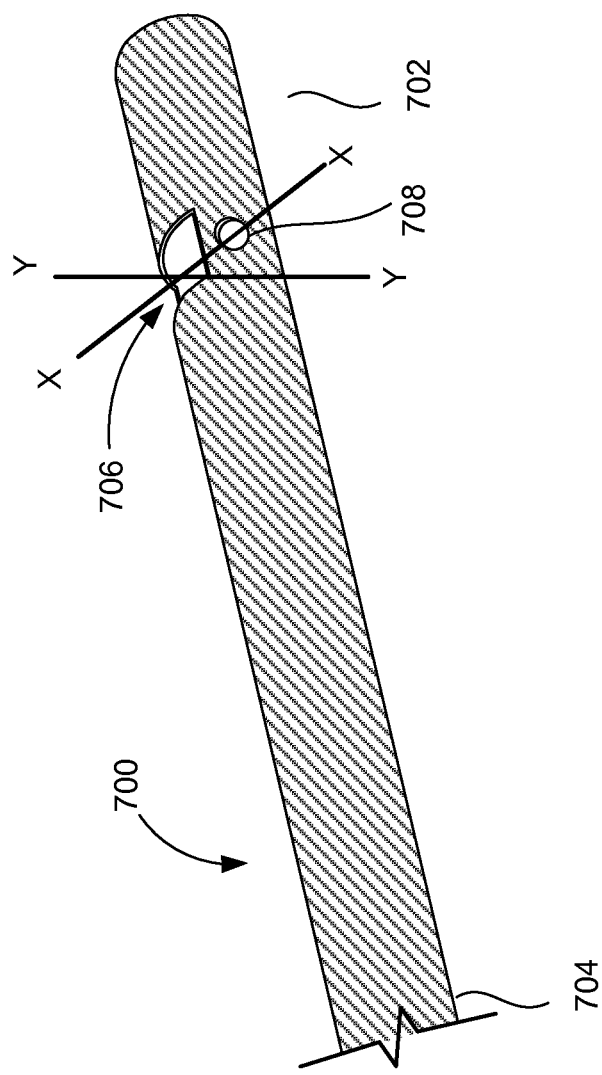
FIG. 7 illustrates an enlarged and isolated partial prospective view of a tubular member of a medical device assembly, according to another embodiment.

FIGS. 5 through 7 illustrate various implementations of the first locking feature of a tubular member of a medical device assembly. FIG. 5 illustrates an enlarged and isolated partial prospective view of a tubular member 500 of a medical device assembly, such as the medical device assembly of FIG. 4, according to one embodiment. In the embodiment of FIG. 5, the tubular member 500 has a distal end 504 and a proximal end 502. The proximal end 502 may be configured to be inserted into or received by a handle of a delivery device, for example delivery device 220. The proximal end 502 may have a first locking feature 506 that includes a first recessed area 508 and a second recessed area 510. In one embodiment, the first recessed area 508 and/or the second recessed area 510 is an aperture or opening in the tubular member. In another embodiment, the first recessed area 508 and/or the second recessed area 510 is a recess or cavity in the sidewall of the tubular member 500. The first recessed area 508 and the second recessed area 510 may be configured to align with a locking member of the delivery device. In some embodiments, the first recessed area 508 and the second recessed area 510 may be on opposite sides of the proximal end 502 of the tubular member 500. Although illustrated as rectangular, it is understood that the first recessed area 508 and the second recessed area 510 may have any shape. Furthermore, it is understood that in some embodiments the tubular member 500 may have more than two recessed areas, depending on the profile of the locking member of the delivery device.

FIG. 6 illustrates an enlarged and isolated partial prospective view of a tubular member 600 of a medical device assembly, such as the medical device assembly of FIG. 4, according to another embodiment. In the embodiment of FIG. 6, the tubular member 600 has a proximal end 602 and a distal end 604. The proximal end 602 may be configured to be inserted into or received by a handle of a delivery device. The proximal end 602 may have a locking feature 606 that includes a single aperture 608. The single aperture 608 may be configured to align with a protrusion or spike that is part of a locking member of the delivery device. Although illustrated as a circular aperture, aperture 608 may have any shape and the shape may depend on the shape or protrusion of the locking member of the delivery device. In an alternative embodiment, the aperture 608 may be an area of penetrable material that allows a sharpened protrusion to embed in the area.

FIG. 7 illustrates an enlarged and isolated partial prospective view of a proximal portion of tubular member of a medical device assembly, such as the medical device assembly of FIG. 4, according to another embodiment. In the embodiment of FIG. 7, the tubular member 700 has a distal end 704 and a proximal end 702. The proximal end 702 may be configured to be inserted into or received in a handle of a delivery device. The proximal end 702 may have a first locking feature that includes a first recessed area 706 and a second aperture 708. The first recessed area 706 and the second aperture 708 may be configured to align with portions of a locking member of the delivery device. For example the first recessed area 706 may align with a first protrusion and the second aperture 708 may align with a second protrusion. In some embodiments, the first recessed area 706 and the second aperture 708 may be on orthogonal planes of the tubular member 700 (e.g., not on opposite sides). In other words, the first recessed area 706 may be aligned with plane Y-Y and the second aperture 708 may be aligned with plane X-X, where X-X and Y-Y are orthogonal. In some embodiments, the first recessed area 706 may be configured to align with a lock catch of the locking mechanism and the second aperture 708 may be configured to align with a protrusion or spike of the locking mechanism of the delivery device.

FIG. 8A illustrates an enlarged and isolated partial perspective view of the medical assembly of FIG. 2, according to an embodiment of the invention. FIG. 8A illustrates the delivery device 220 coupled with the first tubular member 206 of medical device assembly 202. In FIG. 8A the needle 224 of the delivery device 220 is inside the tubular member 206 and, thus, not visible. The locking member 228 of the delivery device 220 is in an unlocked configuration. In other words, a first end 802 of the locking member 228 protrudes from the handle 222, while a second end 804 of the locking member 228 is substantially flush with the handle 222. When the locking member 228 is in the unlocked configuration, as illustrated in FIG. 8A, the tubular member 206 may move or slide freely through the opening defined by the locking member 228.

FIG. 8B illustrates an enlarged and isolated partial perspective view of the medical assembly of FIG. 2 in a locked configuration, according to an embodiment of the invention. FIG. 8B illustrates the delivery device 220 coupled with the first tubular member 206 of medical device assembly 202. In FIG. 8B the needle 224 of the delivery device 220 is inside the tubular member 206 and, thus, not visible. The locking member 228 of the delivery device 220 is in a locked configuration. In other words, a first end 802 of the locking member 228 is substantially flush with the handle 222, while a second end 804 of the locking member 228 protrudes from the handle 222. When the locking member 228 is in the locked configuration, as illustrated in FIG. 8B, the locking member 228 prevents the tubular member 206 from being removed from the locking member 228.

Figure 9A:
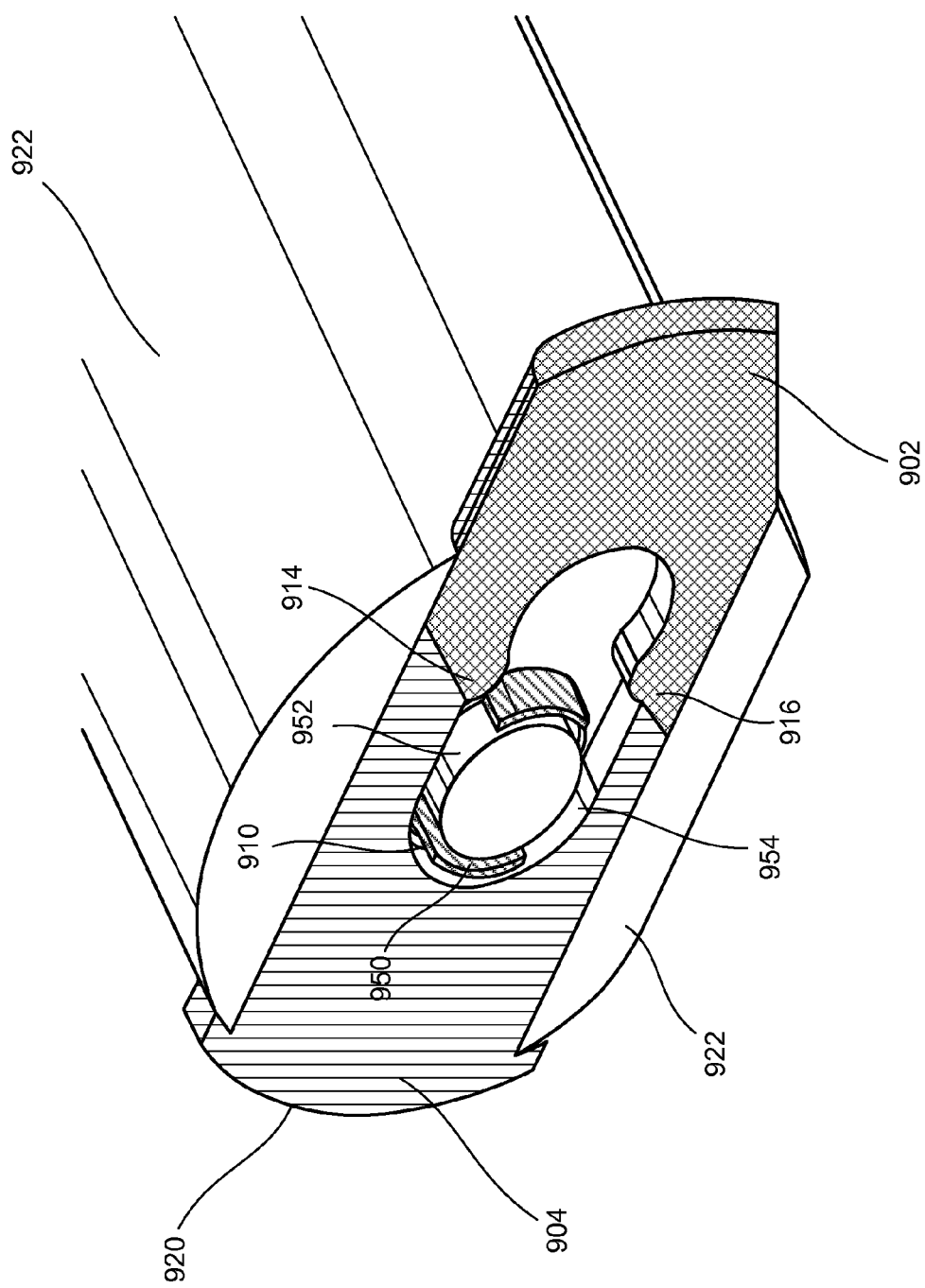
FIG. 9A illustrates a perspective view of an inner-profile of the medical assembly of FIG. 8A along line along line A-A, according to an embodiment.

FIG. 9A illustrates a perspective view of the medical assembly of FIG. 8A along line A-A, according to an embodiment. In the example of FIG. 9A, the locking member 228 of the delivery device 220 includes a sliding member 920 having a first end 902 and a second end 904. The first end 902 may be configured to protrude from the handle 922 of the delivery device when the locking member is in the unlocked configuration. The sliding member 920 may define an opening with a wider portion 910 and a narrower portion 912. In the example of FIG. 9A the sliding member 920 may include a first protrusion 914 and a second protrusion 916. The first protrusion 914 and the second protrusion 916 may be configured to engage a first locking feature of the tubular member 950. In other words, the first protrusion 914 and the second protrusion 916 may be configured to couple with or engage the first locking feature. For example, the tubular member 950 may include a recessed area 952 that allows the first protrusion 914 to slide across the tubular member. In some embodiments, the recessed area 952 is an aperture and the first protrusion 914 may be configured to fall into the aperture in the tubular member 950. In some embodiments, the recessed area 952 is a recess or cavity in the sidewall of the tubular member 950 and the first protrusion 914 may be configured to slide across the recess or cavity. The second protrusion 916 may be similarly configured to couple with a second recessed area 954 on an opposite side of the tubular member 950. In some embodiments, the sliding member 920 may include only one protrusion and the tubular member 950 may include only one recessed area. The first protrusion 914 and the second protrusion 916 may be lock catches configured to prevent the sliding member 920 from moving from the locked configuration to the unlocked configuration absent pressure from an operator of the delivery device on the second end 904.

Figure 9B:
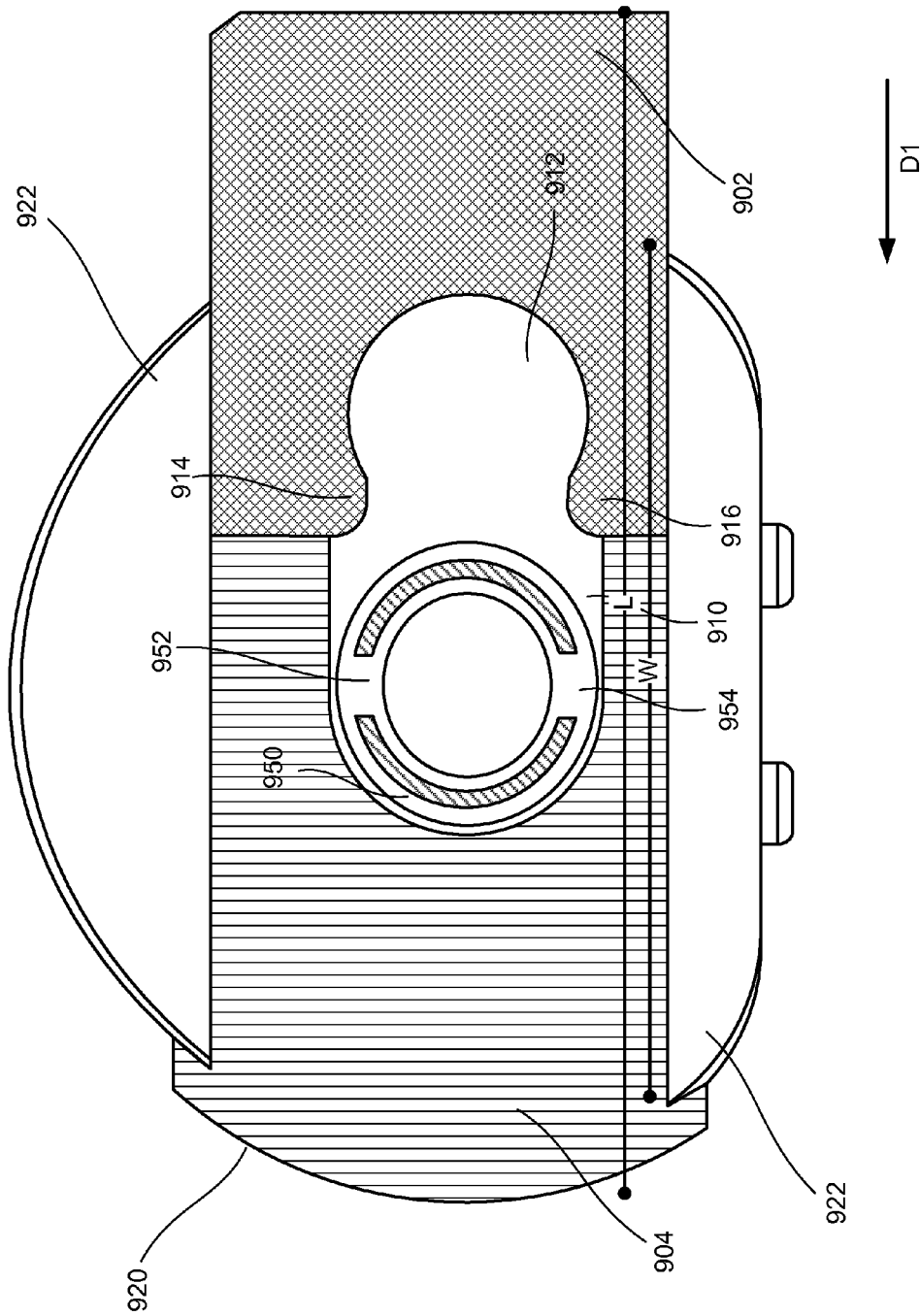
FIG. 9B illustrates a front view of an inner-profile of the medical assembly of FIG. 8A along line A-A, according to an embodiment.

FIG. 9B illustrates a perspective view of an inner-profile of the medical assembly of FIG. 8A along line A-A, according to an embodiment. In the example of FIG. 9B, the locking member 228 of the delivery device 220 includes a sliding member 920 having a first end 902 and a second end 904, as discussed above with regard to FIG. 9A. The sliding member 920 may also include a first protrusion 914 and a second protrusion 916. The first protrusion 914 and the second protrusion 916 may be configured to engage a first locking feature of the tubular member 950, as described above with regard to FIG. 9A. The sliding member 920 may define an opening with a wider portion 910 and a narrower portion 912. The wider portion 910 may be sized so that a tubular member 950 of a medical device assembly, such as a sling assembly, may move freely through the wider portion 910. In other words, the wider portion 910 of the opening may permit free axial movement of the tubular member 950 along the needle 924 of the delivery device. On the other hand, the narrower portion 912 of the opening defined by the sliding member 920 may be sized to frictionally retain the tubular member 950. The sliding member 920 may be configured so that the tubular member 950 aligns with the wider portion 910 when the sliding member 920 is in the unlocked configuration and the tubular member 950 aligns with the narrower portion 912 when the sliding member 920 is in the locked configuration. An operator of the delivery device may move the sliding member 920 from the unlocked configuration to a locked configuration by pressing the first end 902 in direction D1. The first protrusion 914 and the second protrusion 916 may be lock catches configured to prevent the sliding member 920 from moving from the locked configuration to the unlocked configuration absent pressure from an operator of the delivery device on the second end 904.

Figure 10:
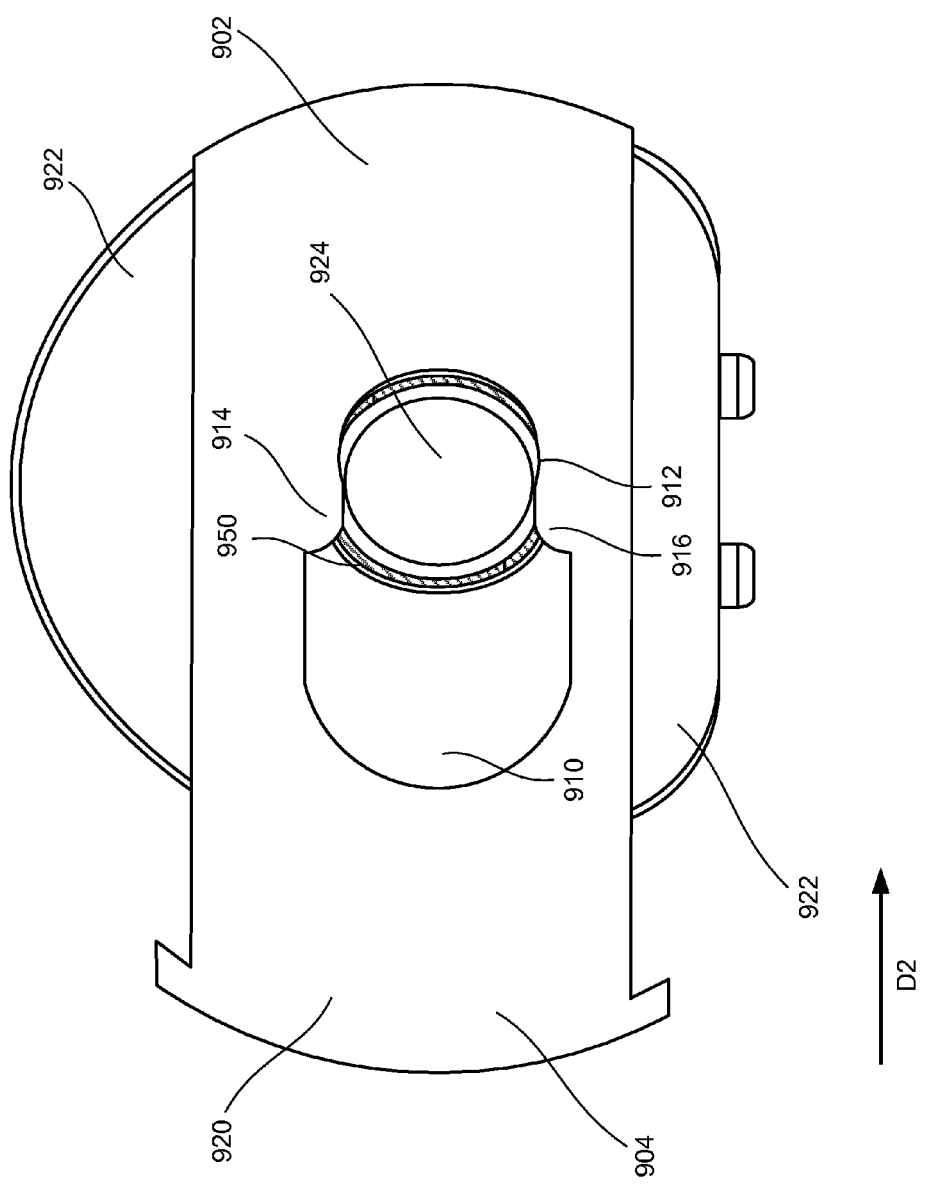
FIG. 10 illustrates a front view of an inner-profile of the medical assembly of FIGS. 9A and 9B in a locked configuration.

FIG. 10 illustrates a perspective view of an inner-profile of the medical assembly of FIG. 9 in a locked configuration, according to an embodiment. In other words, FIG. illustrates the inner-profile of the medical assembly of FIG. 8B along line B-B, according to an embodiment. FIG. 10 illustrates the wider portion 910 and the narrower portion 912 defined by the sliding member 920. FIG. 10 also illustrates that the second end 904 protrudes from the handle 922 when in the locked configuration, while the first end 902 is substantially flush with the handle 922. In the example of FIG. 10, the first end 902 has a visual appearance that differs from the visual appearance of the second end 904. For example, the first end 902 may appear green and the second end 904 may appear red. Also illustrated in FIG. 10, the first protrusion 914 and the second protrusion 916 couple with the locking feature of the tubular member 950. When coupled, the sliding member 920 prevents axial movement of the tubular member 950, e.g., movement along the needle 924. Preventing axial movement prevents the tubular member 950 from being removed from the locking member and, thus, from the handle 922 of the delivery device. An operator of the delivery device may move the sliding member 920 from the locked configuration to an unlocked configuration by pressing the second end 904 in direction D2.

Figure 11:
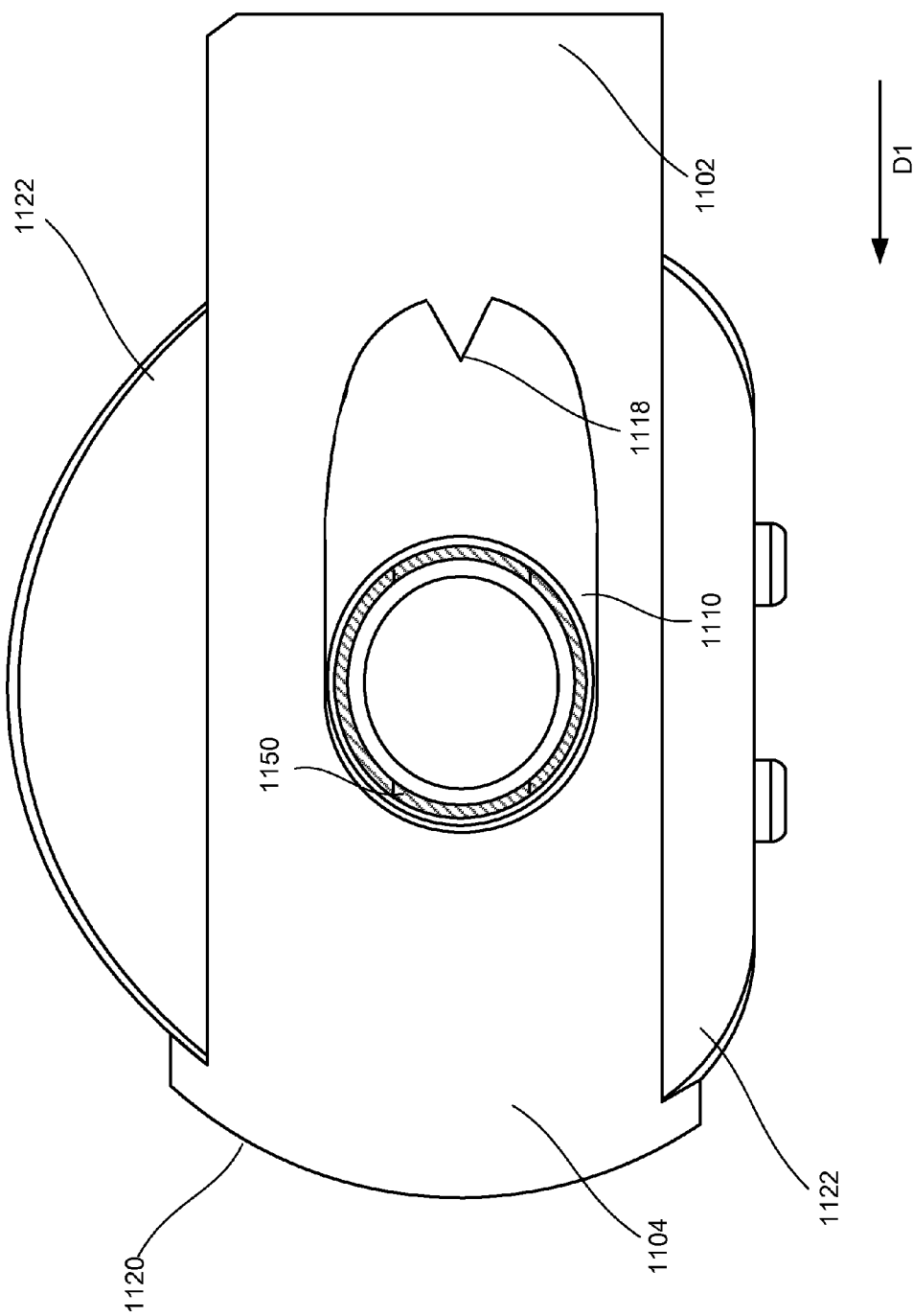
FIG. 11 illustrates a front view of an inner-profile of a medical assembly, according to another embodiment.

FIG. 11 illustrates a perspective view of an inner-profile of the medical assembly according to another embodiment. In the example of FIG. 11, the locking member of the delivery device includes a sliding member 1120 having a first end 1102 and a second end 1104. The first end 1102 may be configured to protrude from the handle 1122 of the delivery device when the locking member is in the unlocked configuration. The sliding member 1120 may define an opening 1110 through which a tubular member 1150 of a medical device assembly, such as a sling assembly, may move freely. In other words, the opening 1110 may be a wide opening that permits axial movement of the tubular member.

The sliding member 1120 may include a first spike or protrusion 1118. The protrusion 1118 may have a length P. In some implementations, the protrusion 1118 may be configured to couple with the tubular member 1150. For example, the spike may be configured to slide into an aperture of the tubular member, but not long enough to pierce the needle 1124 of the delivery device. In another embodiment, the tubular member 1150 may be made of flexible or penetrable material, or have an area of penetrable material, and the protrusion 1118 may be configured to imbed into the tubular member 1150. In some embodiments the sliding member 1120 may include two or more such protrusions 1118. An operator of the delivery device may move the sliding member 1120 from the unlocked configuration to a locked configuration by pressing the first end 1102 in direction D1.

Figure 12:
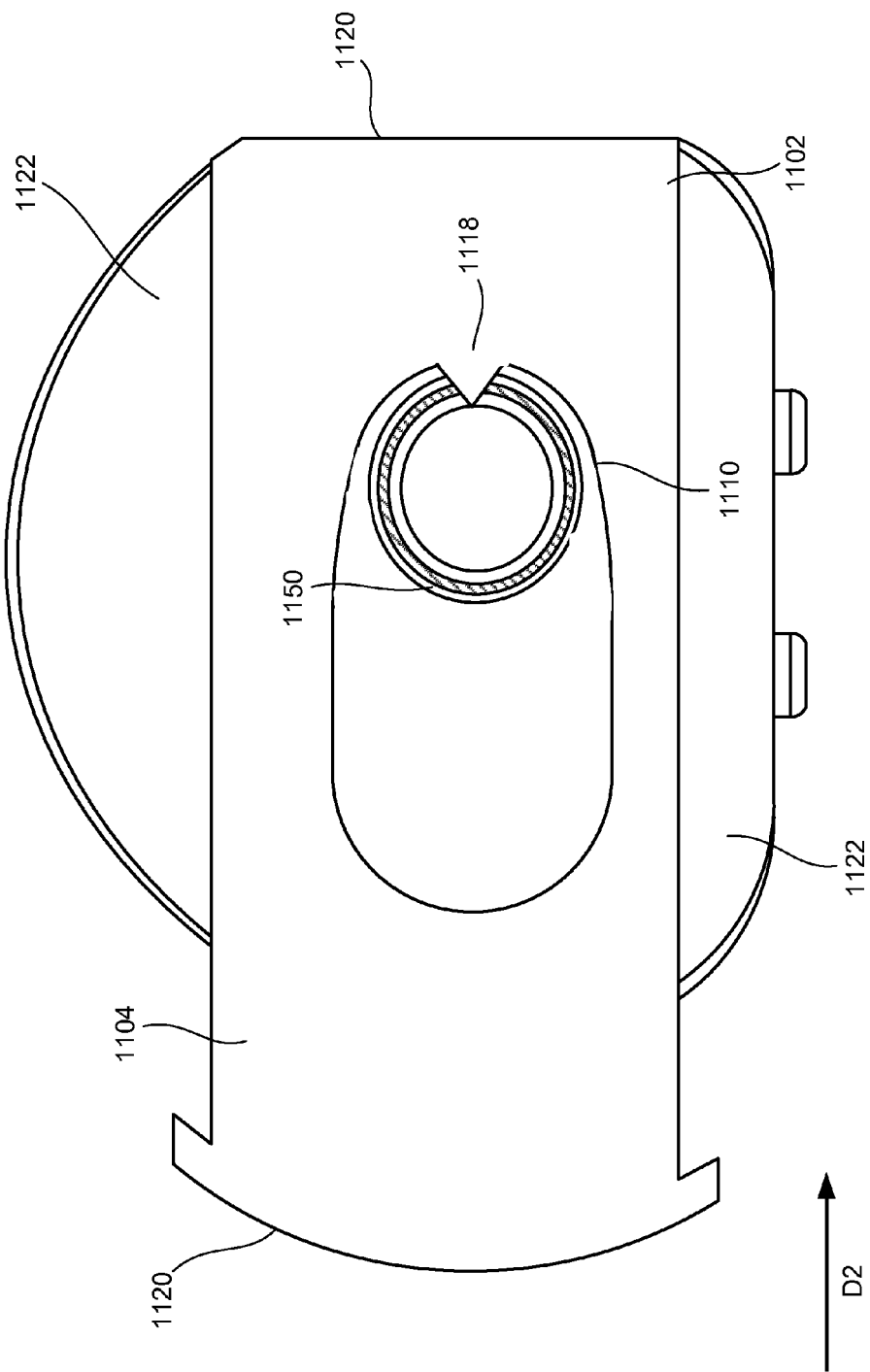
FIG. 12 illustrates a front view of an inner-profile of the medical assembly of FIG. 11 in a locked configuration.

FIG. 12 illustrates a perspective view of an inner-profile of the medical assembly of FIG. 11 when the locking member is moved to a locked configuration, according to an embodiment. FIG. 12 illustrates that the second end 1104 protrudes from the handle 1122 when in the locked configuration, while the first end 1102 is substantially flush with the handle 1122. In the example of FIG. 12, the first end 1102 has a visual appearance that differs from the visual appearance of the second end 1104. For example, the first end 1102 may appear green and the second end 1104 may appear red. Also illustrated in FIG. 12, the protrusion 1118 may imbed in tubular member 1150 or may slide into an opening configured to receive the protrusion 1118. In some embodiments, the opening may be configured to create a friction fit between the protrusion 1118 and the opening. When the protrusion 1118 imbeds in the tubular member 1150 or is received into the opening in the tubular member, the sliding member 1120 prevents axial movement of the tubular member 1150, e.g., movement along the needle 1124. Preventing axial movement prevents the tubular member 1150 from being removed from the locking member and, thus, from the handle 1122 of the delivery device. An operator of the delivery device may move the sliding member 1120 from the locked configuration to an unlocked configuration by pressing the second end 1104 in direction D2. In some embodiments, the locking member may include a lock catch that prevents the sliding locking member from moving from the locked configuration to the unlocked configuration absent pressure on the second end 1104 in the direction of D2.

Figure 13:
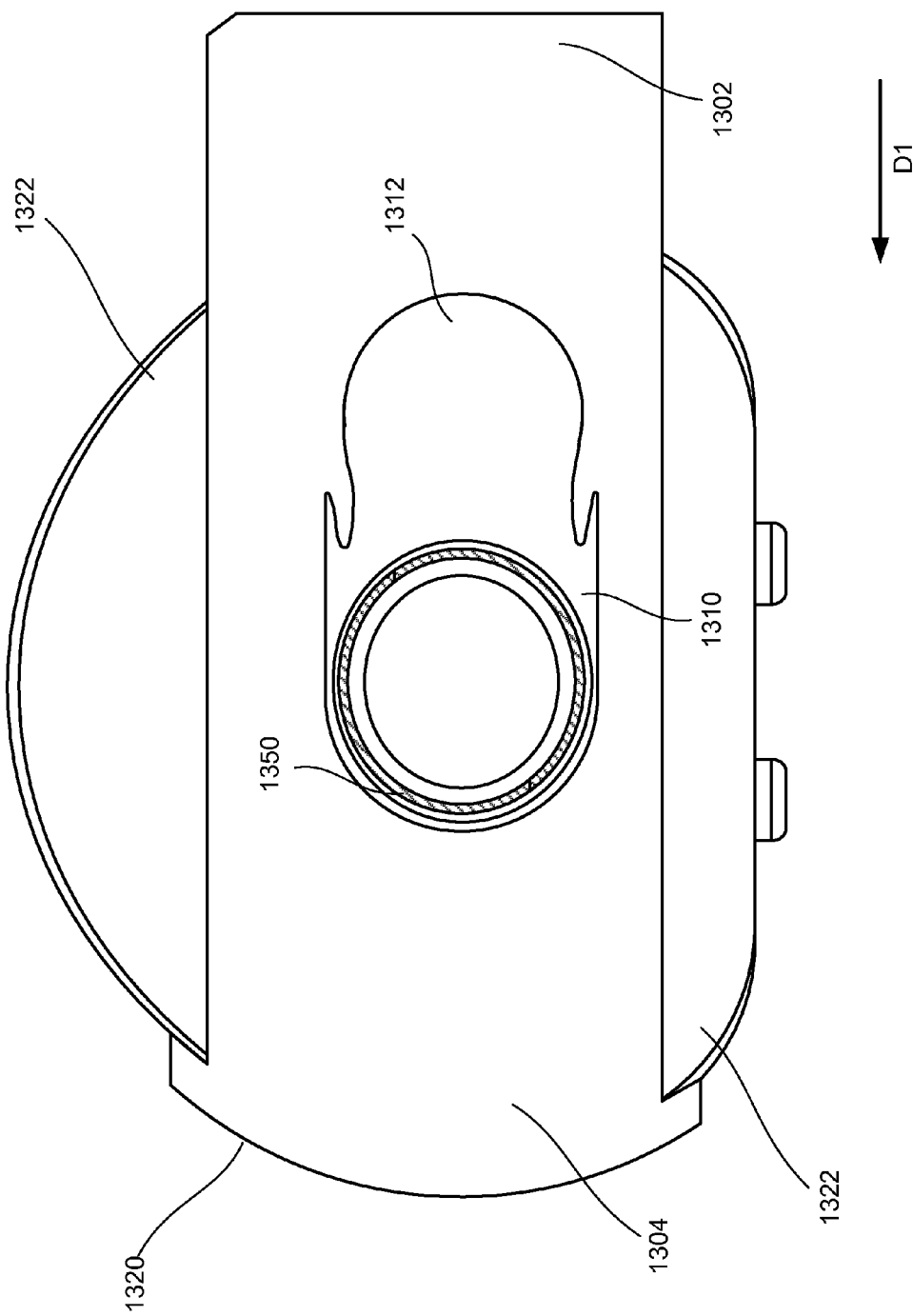
FIG. 13 a front view of an inner-profile of a medical assembly, according to another embodiment.

FIG. 13 illustrates a perspective view of an inner-profile of the medical assembly with a locking member in an unlocked configuration, according to another embodiment. In the example of FIG. 13, the locking member includes a sliding member 1320 having a first end 1302 and a second end 1304. The first end 1302 may be configured to protrude from the handle 1322 of the delivery device when the locking member is in the unlocked configuration. The sliding member 1320 may define an opening that includes a wider portion 1310 and a narrower portion 1312. The wider portion 1310 is configured to allow a tubular member 1350 to freely pass through the locking member when the locking member is in the unlocked configuration. In other words, the wider portion 1310 permits axial movement of the tubular member 1350 through the sliding member 1320. The narrower portion 1312 of the opening defined by the sliding member 1320 may be configured to provide a friction fit with the tubular member 1350. For example, the narrower portion 1312 may be sized to create an interference fit by pinching down on the tubular member 1350. In some embodiments, the locking member may be made of a flexible material that expands slightly to create the interference fit. An operator of the delivery device may move the sliding member 1320 from the unlocked configuration to a locked configuration by pressing the first end portion 1302 in direction D1.

Figure 14:
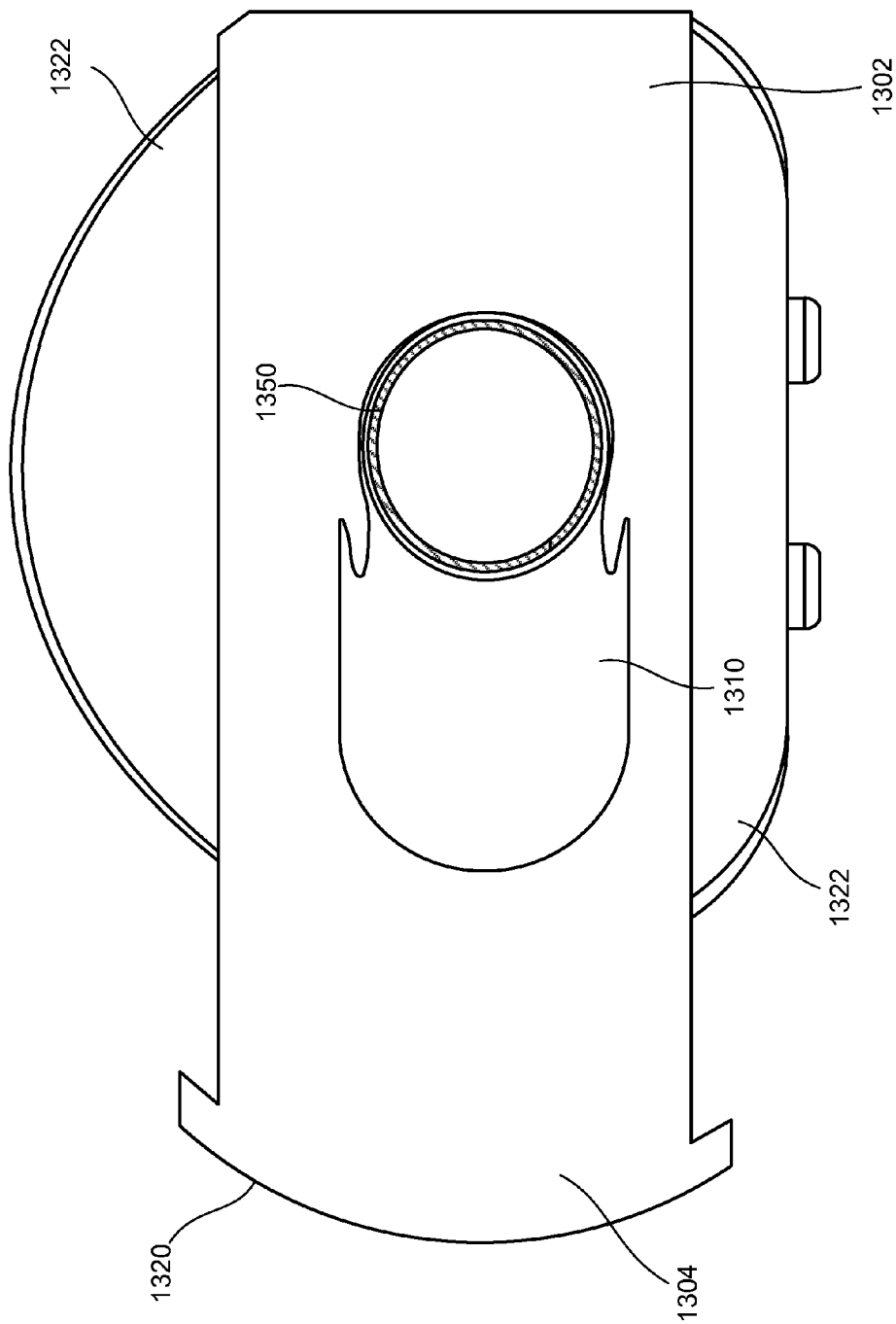
FIG. 14 illustrates a front view of an inner-profile of the medical assembly of FIG. 11 in a locked configuration.

FIG. 14 illustrates a perspective view of an inner-profile of the medical assembly of FIG. 13 when the locking member is moved to a locked configuration, according to an embodiment. FIG. 14 illustrates that the second end 1304 protrudes from the handle 1322 when in the locked configuration, while the first end 1302 is substantially flush with the handle 1322. In the example of FIG. 14, the first end 1302 has a visual appearance that differs from the visual appearance of the second end 1304. For example, the first end 1302 may appear green and the second end 1304 may appear red. Also illustrated in FIG. 14, the narrower portion 1312 of the opening defined by the sliding member 1320 may form an interference fit by pinching down on the tubular member 1350. The interference fit may prevent axial movement of the tubular member 1350, e.g., movement along the needle 1324. Preventing axial movement prevents the tubular member 1350 from being removed from the locking member and, thus, from the handle 1322 of the delivery device. An operator of the delivery device may move the sliding member 1320 from the locked configuration to an unlocked configuration by pressing the second end 1304 in direction D2.

FIG. 15 illustrates a cross-section view of the medical assembly of FIG. 8A along line C-C, according to an embodiment. In the example of FIG. 15, the medical assembly includes tubular member 206, and a delivery device 220 with a handle 222. The distal end of the handle 222 may include a locking member 228. The locking member 228 may have a locked configuration and an unlocked configuration. In the unlocked configuration, the locking member 228 may allow the tubular member 206 to pass through the locking member. The handle 222 may also include a stop 1502 that prevents the tubular member 206 from entering any further into the handle 222. The stop 1502 may be positioned in the handle so that when the tubular member 206 abuts the stop, a locking feature on the tubular member 206 aligns with the locking member 228 of the delivery device 220. Thus, stop 1502 may assist an operator in aligning the locking feature of the tubular member 206 with the locking member 228.

Figure 16A:
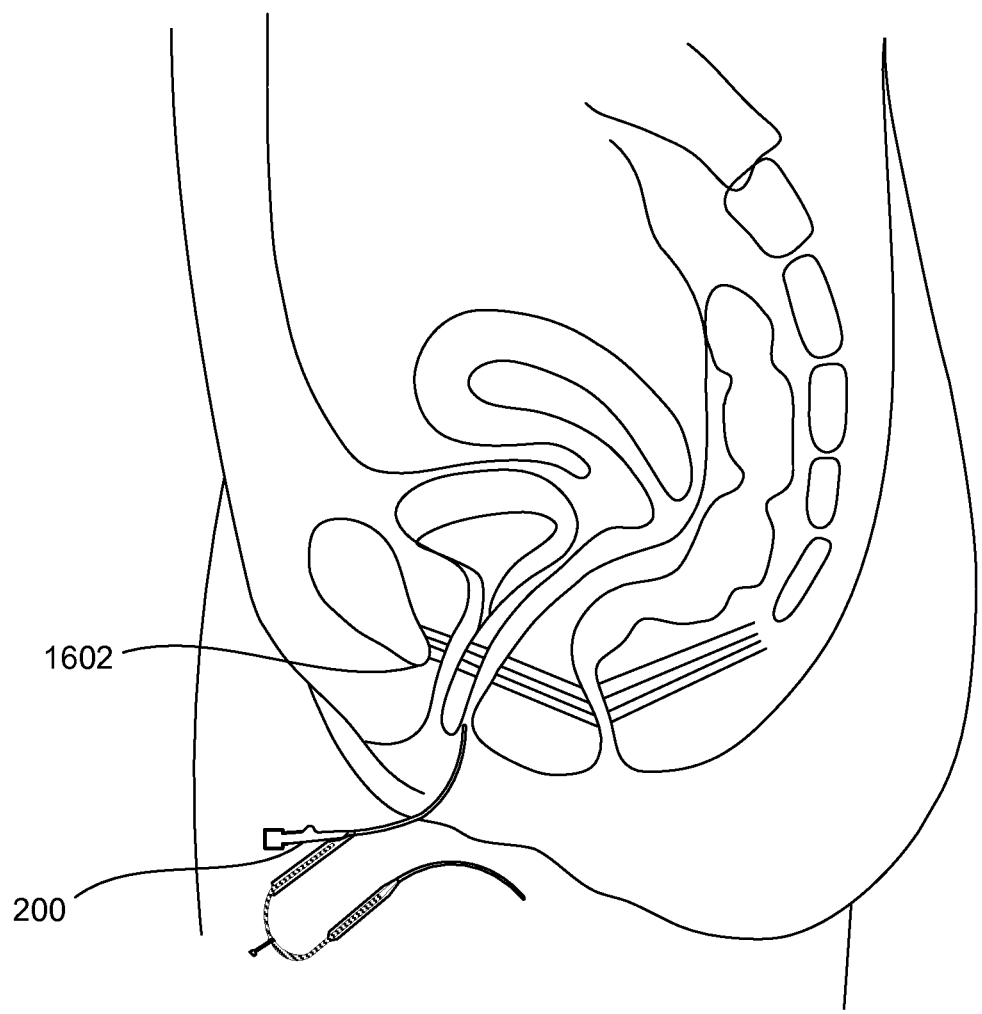
FIG. 16A illustrates positioning of a medical assembly inside a female body through a vaginal approach.

FIG. 16A illustrates positioning of a medical assembly 200 inside a female body through a vaginal approach. The method of positioning the medical assembly 200 includes coupling a tubular member of a medical device assembly, for example a sling assembly, with a delivery device that has a locking member in an unlocked configuration and moving the locking member to a locked configuration once the tubular member has passed through an opening in the locking member. The operator of the medical assembly 200 may create a vaginal incision in the vaginal space 1602 and move the tubular member into position within the pelvic floor region. The operator may position the medical device at a first location and unlock the locking member of the delivery device so that the delivery device may be removed. The operator may couple a tubular member on a second end of the medical device assembly with a delivery device, move the locking member of the delivery device to a locked configuration and position the second end at a second location within the pelvic floor region. The operator may then unlock the locking mechanism and remove the delivery device.

Figure 16B:
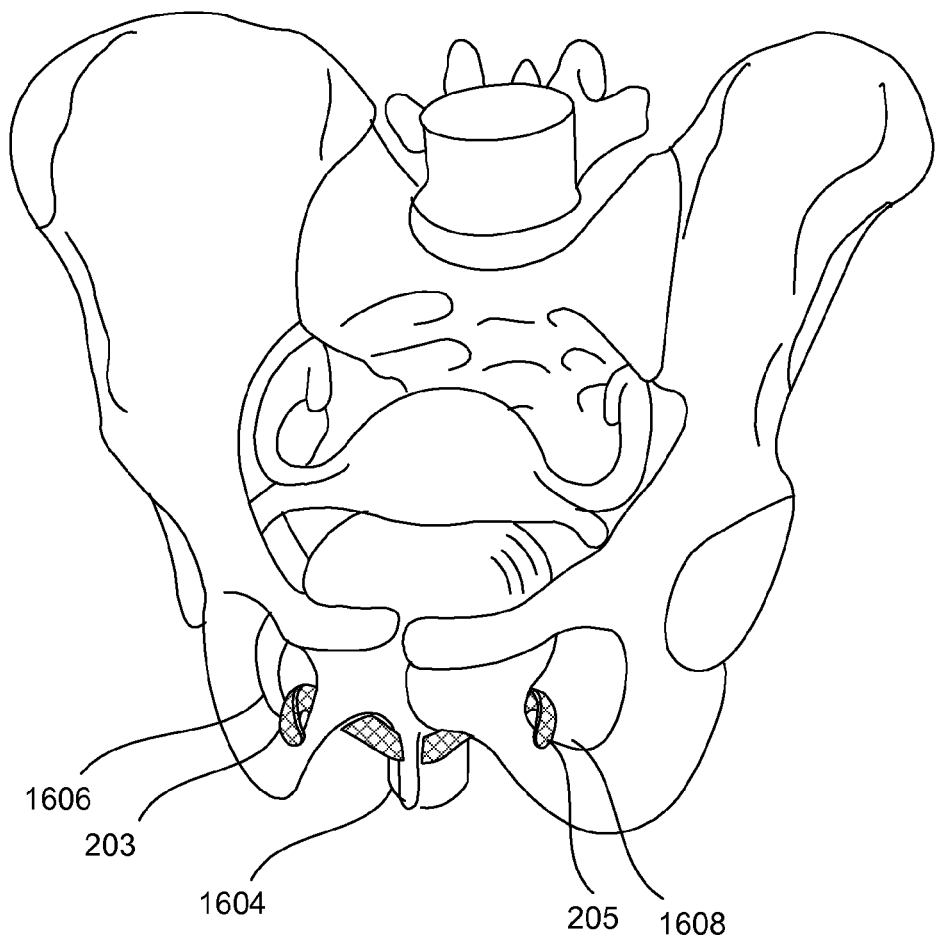
FIG. 16B illustrates implantation of an implant inside a female body through a transobturator approach.

FIG. 16B illustrates implantation of the implant 204 inside a female body through a transobturator approach. In accordance with this approach, the implant 204 is passed under the urethra 1604 and out through incisions in a groin compartment of the thigh (not shown in the diagram). The implant 204 can be attached at the first end portion 203 at a first location 1606 within the pelvic floor region. The second end portion 205 of the implant 204 can be attached at a second location 1608 within the pelvic floor region. In an embodiment, the first location 1606 and the second location 1608 can be the obturator foreman tissues proximate the obturator foreman.

Figure 17:
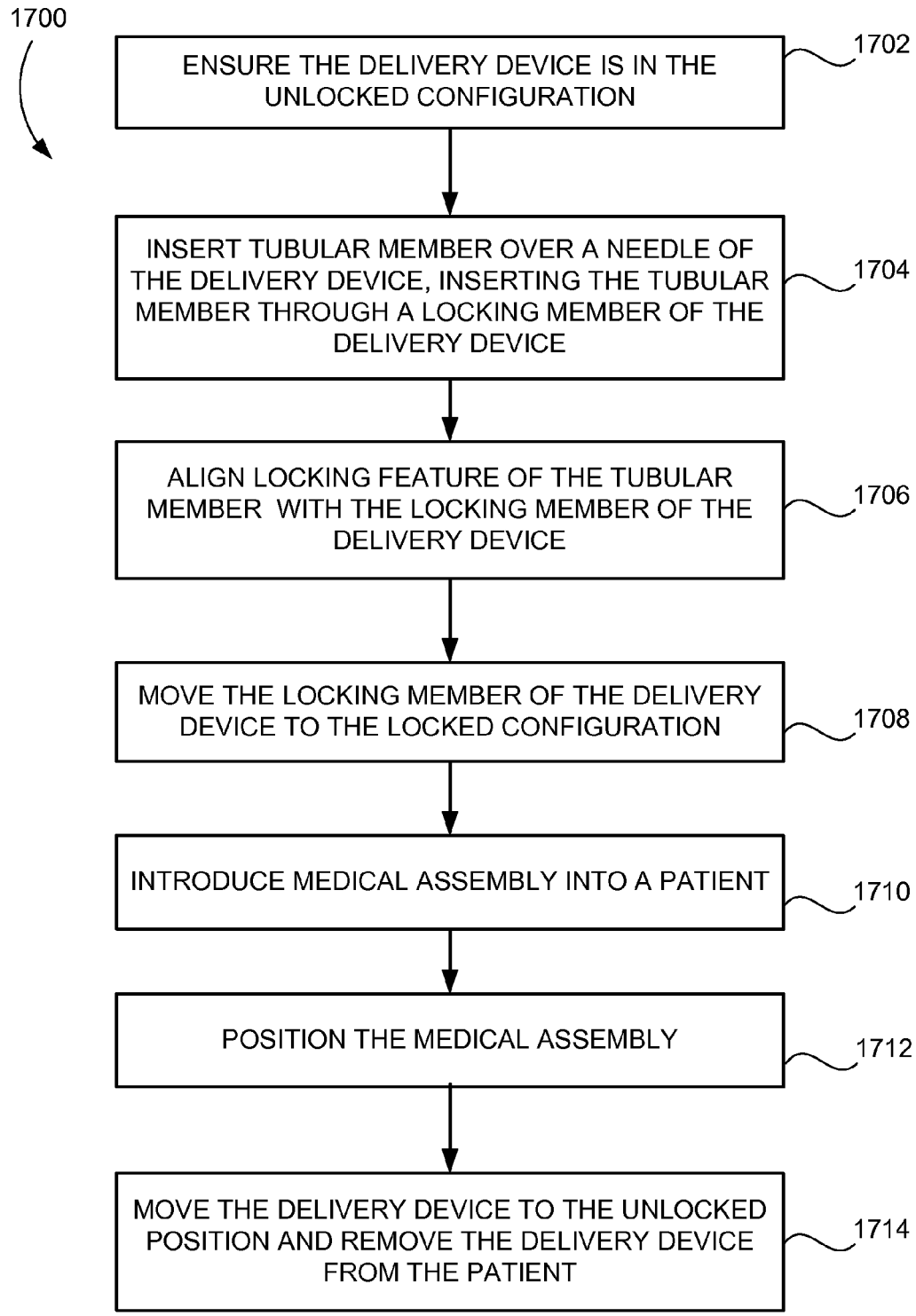
FIG. 17 illustrates a flowchart representing a method for delivery of a medical assembly in a patient's body, in accordance with an embodiment.

FIG. 17 illustrates a flowchart representing a method 1700 for delivery of a medical device assembly such as the medical device assembly 102 or 202 in a patient's body. For example, the medical device assembly may be for treatment of a pelvic floor disorder. In an embodiment, the pelvic floor region can be a retropubic region. Referring to FIG. 17, in conjunction with FIG. 2, the method of delivery and placement of the implant 204 with the use of the delivery device 220 is described in accordance with an embodiment of the present invention. The medical device assembly 202 is described as a sling assembly, but it is understood that that other medical device assemblies such as the medical device assembly 102 may also be employed in a similar manner.

The method 1700 includes ensuring that the locking member of the delivery device is an unlocked configuration (1702). In some embodiments, a first end portion of the locking member may have a first visual appearance, for example green, and a second end portion of the locking member may have a second visual appearance, for example red. The operator of the delivery device may ensure the locking member is in the unlocked configuration if the first end portion protrudes from the handle of the delivery device and the second end portion is substantially flush with the handle. In some embodiments this may include verifying that the portion protruding from the handle has the first visual appearance, e.g., the protruding portion is green. The method also includes inserting a tubular member of the medical device assembly over a needle of the delivery device and inserting the tubular member into a locking member of the delivery device (1704). The method also includes aligning the first locking feature of the tubular member with the locking member of the delivery tool (1706). In some embodiments, the handle may include a stop that helps align the locking feature of the tubular member with the locking member of the delivery tool. In some embodiments, the proximal portion of the tubular member may include a guide that aligns with a guide in the distal portion of the handle. For example, the tubular member may include a trench that aligns with a tab on the handle of the delivery tool. Aligning the locking member with the locking feature may also include applying a small amount of pressure on the first end of the locking member in the handle of the delivery device and rotating the tubular member until the locking member begins to move from the unlocked configuration into the locked configuration.

The method also includes moving the delivery device into the locked configuration (1708). For example, the operator of the delivery device may apply pressure to the first end portion of the locking member until the first end portion is substantially flush with the handle of the delivery tool and the second end portion protrudes from the handle. With the tubular member secured by the locking member, the operator may introduce the medical assembly into the patient (1710). In an embodiment, the method may include creating a vaginal incision for delivery of the delivery device 220 and the tubular member 206 within the body through a transvaginal approach. The locking member in the locked configuration secures the tubular member 206 to the delivery device 220 allowing the operator to control and direct the needle 224 by means of the tubular member 206 positioned over the needle 224. In an embodiment, the medical assembly 200 can be pre-assembled and the operator may not be required to perform the step of assembling (e.g., steps 1702 to 1708).

Once the tubular member 206 is secured to the handle 222 via the locking member 228, the operator can grasp the tubular member 206 to manipulate the delivery device 220 into, about and through the patient. Once the tubular member 206 and the needle 224 are inserted through the patient, the method includes positioning of the implant 204 at the target location, for example the pelvic floor region. Upon reaching of the implant 204 at its target location, the operator then moves the locking member 228 of the delivery device 220 from the locked position to the unlocked position (1714). In an embodiment, moving the locking member 228 from a locked configuration to an unlocked configuration may include applying pressure to a second end of the locking member 228 that protrudes from the handle 222 of the delivery device 220 until the second end is substantially flush with the handle 222. In some embodiments, this movement causes a first end of the locking member 228 to protrude from the handle 222. The first end may have a first visual appearance that indicates to the operator that the locking member 228 is in the unlocked configuration. The operator may then freely disassociate the delivery device 220 from the tubular member 206 and remove the delivery device 220, including the needle 224, from the patient. In some embodiments, the operator may repeat method 1700 on a second end portion 205 of the implant 204, for example using a second tubular member 216 and positioning the second end portion 205 at a second location in the pelvic floor region, as discussed above with regard to FIGS. 16A and 16B.

In an embodiment, a delivery device similar to the delivery device 220 can be coupled to a second tubular member 216 in a manner similar to that described above. In another embodiment, the delivery device 220 can be coupled to the second tubular member 216 to implant the second end portion 205 to the target tissue location.

The method may further include removing the tubular member 206 from the patient's body after disassociating the tubular member 206 from the delivery device 220 once the delivery device 220 reaches the target body location in the pelvic floor region. The operator may also disassociate the first sleeve 218 by cutting a suture, wherein the suture couples the first sleeve 218 with the tubular member 206. In an embodiment, the tubular member 206 and the first sleeve 218 can be removed from the implant 204. The first sleeve 218 and the first tubular member 206 can then be pulled out from the patient's body through incisions such as provided in an abdomen or in a groin or an obturator area of the patient. The second tubular member 216 can also be removed in a similar manner. In some embodiments, separate sutures may be used to couple the sleeves to the implant.

Upon implanting the implant 204 at the target location, the operator may fix the implant at a first portion within the pelvic floor region. In an embodiment, the pelvic floor region is a retropubic region. The method further comprises attaching the first end portion 203 and the second end portion 205 of the implant 204, respectively, at a first portion and a second portion within the pelvic floor region of the patient, as described in FIG. 11B.

In some embodiments, the medial assembly as described above may be used in portions or locations within the body other than the pelvic region of the patient. For example, the medial assembly may be used to insert and implant and provide support to any portion of a body of a patient.

FIG. 18 illustrates a side view of an inner-profile of a medical assembly, according to an embodiment. The medical assembly 1800 may be an example of medical assembly 100 of FIG. 1. The medical assembly 1800 may include a delivery device 1820 and a medical device assembly that includes a tubular member 1806. The medical device assembly may be an example of the medical device assembly 102 of FIG. 1. The delivery device 1820 may be configured for placing the medical device assembly within a body of a patient. The delivery device 1820 may include a handle 1822, a needle 1824, and a locking member 1828. In an embodiment, the needle 1824 can be a surgical needle with a substantially small outer diameter for minimally invasive surgery. The needle 1824 may be configured to be inserted into the tubular member 1806 of a medical device assembly, and may be one example of tubular member 106 of medical device assembly 102.

The delivery device 1820 may also be configured to receive a proximal portion 1808 of the tubular member 1806 into a cavity 1842 defined by the handle 1822, for example at the distal portion 1830 of the handle 1822. The locking member 1828 of the delivery device 1820 may be a tapered sidewall of the handle 1822 that defines cavity 1842. In other words, as the cavity extends from the distal portion 1830 of the handle 1822 in direction D3, the cavity 1842 between the handle 1822 and the needle 1824 decreases in size. The tubular member 1806 may be coupled to the delivery device 1820 via a friction fit between a distal end of the tubular member 1806 and the tapered sidewall, e.g., the locking member 1828, of the delivery device 1820. Thus, in the example of FIG. 18, the tubular member 1806 lacks a first locking feature. The tubular member 1806 may be made of a resilient or flexible material that deforms slightly to achieve the friction fit. An operator of the delivery device 1820 may achieve a friction fit by sliding the tubular member 1806 over the needle 1824 and into cavity 1842 of the handle 1822. The operator may apply pressure, or move, the tubular member 1806 in direction D3 and or move the handle 1822 in direction D4 to achieve the friction fit. To uncouple the tubular member 1806 from the handle 1822, the operator may slide or move the tubular member in direction D4 and/or move the handle 1822 in direction D3.

One illustrative embodiment discloses a delivery device having a handle having a proximal portion and a distal portion, wherein the distal portion of the handle is coupled to a proximal portion of a needle and the distal portion of the handle is configured to accept a proximal portion of a tubular member of a medical device assembly. The distal portion of the handle includes a locking member, the locking member being configured to be placed in a locked configuration and an unlocked configuration, the locking member having a first end and a second end and defining an opening. The opening may be configured to allow a proximal portion of the tubular member to pass through the locking member when the locking member is in the unlocked configuration and configured to prevent the tubular member from being removed from the locking member when the locking member is in the locked configuration. When in the locked configuration, the locking member ensures the tubular member stays intact with the delivery device, preventing premature or inadvertent release of the tubular member. The first end of the locking member may protrude from a first side of the handle when the locking member is in the unlocked configuration and the second end may protrude from a second side of the handle when the locking member is in the locked configuration. In addition, the first end of the locking member may have a first visual appearance and the second end may have a second visual appearance that enables an operator of the delivery device to ensure that the locking member is in an unlocked or locked configuration, respectively. The first visual appearance may be one color, for example green and the second visual appearance may be another color, for example red. In addition or alternatively, the first visual appearance may include a first image and the second visual appearance may include a second image.

In addition or alternatively, the locking member may be configured to slide from the unlocked configuration to the locked configuration in response to pressure on the first end and configured to slide from the locked configuration to the unlocked configuration in response to pressure on the second end.

In some embodiments, the locking member includes a protrusion proximate the first end, the protrusion configured to couple with a first locking feature of the tubular member when the locking member is in the locked configuration. In addition or alternatively, the locking member may also include a protrusion proximate the first end configured to imbed at least partially into the tubular member when the locking member is in the locked configuration. In addition or alternatively, the locking member includes a first protrusion proximate the first end, the first protrusion configured to slide into an aperture defined by the tubular member when the locking member is moved from the unlocked configuration to the locked configuration. In addition or alternatively, the opening includes a narrower portion proximate the first end of the locking member and a wider portion proximate the second end of the locking member, the narrower portion configured to prevent, via a friction fit, the tubular member from being removed and the wider portion configured to permit free axial movement of the tubular member.

Another illustrative embodiment discloses a medical assembly that includes an implant for placement in a body of a patient, a tubular member configured to be coupled to the implant and including a proximal portion and a distal portion, the proximal portion defining a first locking feature, and a delivery device configured to deliver the implant. The delivery device includes a needle having a proximal portion and a distal portion such that the tubular member is positioned over the needle, and a handle having a proximal portion and a distal portion, wherein the distal portion of the handle is coupled to the proximal portion of the needle and the distal portion of the handle is configured to accept the proximal portion of the tubular member. The delivery device also includes a locking member in the distal portion of the handle, the locking member being configured to be placed in a locked configuration and an unlocked configuration, the locking member defining an opening, the opening being configured to allow at least a portion of the tubular member to pass through the locking member when the locking member is in the unlocked configuration and the locking member configured to engage the first locking feature of the tubular member to prevent the tubular member from being removed from the locking member when the locking member is in the locked configuration.

In addition, the locking member may have a first end that protrudes from a first side of the handle when the locking member is in the unlocked configuration and a second end that protrudes from a second side of the handle when the locking member is in the locked configuration. In addition, the first end may have a first visual appearance and the second end may have a second visual appearance that differs from the first visual appearance. In addition or alternatively, the first visual appearance can be green and the second visual appearance can be red.

In addition or alternatively, the first locking feature may be an aperture and the locking member can further include a protrusion configured to couple with the first locking feature of the tubular member when the locking member is in the locked configuration. In addition or alternatively, the first locking feature may be an aperture and the locking member may further include a protrusion configured to slide into the first locking feature of the tubular member when the locking member is in the locked configuration. In addition or alternatively, the first locking feature may be a penetrable material and the locking member may further include a protrusion configured to imbed into the penetrable material when the locking member is in the locked configuration. In addition or alternatively, the opening may include a narrower portion proximate a first end of the locking member and a wider portion proximate a second end of the locking member, the narrower portion configured to prevent the locking member from moving from the locked configuration to the unlocked configuration absent pressure applied to the second end of the locking member.

Another illustrative embodiment discloses a method for treatment of a pelvic floor disorder in a patient's body. The method includes ensuring a locking member of a delivery device is in an unlocked configuration, the locking member being in a distal end of a handle of the delivery device and the unlocked configuration indicated by a first end of the locking member protruding from a first side of the handle and a second end of the locking member opposite the first end being substantially flush with a second side of the handle. The method also includes inserting a tubular member of a medical device assembly over a needle of the delivery device and through an opening defined by the locking member, the medical device assembly including an implant and moving the locking member from the unlocked configuration to a locked configuration, the locked configuration preventing the tubular member from being removed from the locking member, the locked configuration indicated by the second end protruding from the second side of the handle and the first end being substantially flush with the first side of the handle. The method also includes inserting the delivery device and the tubular member inside the patient's body, disassociating the tubular member from the delivery device once the delivery device reaches a target body location in a pelvic floor region by placing the locking member into the unlocked configuration, and fixing the implant at a first location within the pelvic floor region.

In some implementations, the first end of the locking member has a first visual appearance and the second end of the locking member has a second visual appearance, the first visual appearance assisting in ensuring that the locking member is in the unlocked configuration and the second visual appearance assisting in ensuring that the locking member is in the locked configuration. In addition or alternatively, the method may include aligning a protrusion of the locking member with a first locking feature of the tubular member prior to ensuring the locking member is moved from the unlocked configuration to the locked configuration.

Another illustrative embodiment discloses a delivery device including a handle having a proximal portion and a distal portion, wherein the distal portion of the handle is configured to be coupled to a proximal portion of a needle and the distal portion of the handle is configured to slideably accept at least a proximal portion of a tubular member of a medical device assembly. The distal portion of the handle also includes a locking member, the locking member being configured to be placed in a locked configuration and an unlocked configuration. The locking member has a first end and a second end and defining an opening. The opening is configured to allow a proximal portion of the tubular member to pass through the locking member when the locking member is in the unlocked configuration and configured to prevent the tubular member from being removed from the locking member when the locking member is in the locked configuration. In addition, the first end protrudes from a first side of the handle when the locking member is in the unlocked configuration and the second end protrudes from a second side of the handle when the locking member is in the locked configuration.

In addition or alternatively, the first end may have a first visual appearance and the second end has a second visual appearance that differs from the first visual appearance. For example, the first end may be green and the second end may be red. In addition or alternatively, the locking member may be configured to slide from the unlocked configuration to the locked configuration in response to pressure on the first end and configured to slide from the locked configuration to the unlocked configuration in response to pressure on the second end. In addition or alternatively, the locking member further may include a protrusion proximate the first end, the protrusion configured to couple with a first locking feature of the tubular member when the locking member is in the locked configuration. In addition or alternatively, the locking member may include a protrusion proximate the first end, the protrusion configured to imbed at least partially into the tubular member when the locking member is in the locked configuration. In addition or alternatively, the locking member may include a first protrusion proximate the first end, the first protrusion configured to slide into an aperture defined by the tubular member when the locking member is moved from the unlocked configuration to the locked configuration. In addition or alternatively, the opening may include a narrower portion proximate the first end of the locking member and a wider portion proximate the second end of the locking member, the narrower portion configured to prevent, via a friction fit, the tubular member from being removed and the wider portion configured to permit free axial movement of the tubular member.

Another illustrative embodiment discloses a medical assembly that includes an implant for placement in a body of a patient, a tubular member configured to be coupled to the implant and including a proximal portion and a distal portion, the proximal portion defining a first locking feature, and a delivery device configured to deliver the implant. The delivery device may include a needle, a handle, and a locking member in the distal portion of the handle. The needle may have a proximal portion and a distal portion such that the tubular member is positioned over the needle. The handle may have a proximal portion and a distal portion, wherein the distal portion of the handle is coupled to the proximal portion of the needle and the distal portion of the handle is configured to accept the proximal portion of the tubular member. The locking member may be configured to be placed in a locked configuration and an unlocked configuration. The locking member also defines an opening, the opening being configured to allow at least a portion of the tubular member to pass through the locking member when the locking member is in the unlocked configuration and the locking member configured to engage the first locking feature of the tubular member to prevent the tubular member from being removed from the locking member when the locking member is in the locked configuration.

In addition or alternatively, the locking member may have a first end that protrudes from a first side of the handle when the locking member is in the unlocked configuration and a second end that protrudes from a second side of the handle when the locking member is in the locked configuration. The first end may have a first visual appearance and the second end may have a second visual appearance that differs from the first visual appearance. For example, the first visual appearance may include a first image and the second visual appearance may include a second image. In addition or alternatively, the first locking feature may be an aperture and the locking member further includes a protrusion configured to couple with the first locking feature of the tubular member when the locking member is in the locked configuration. In addition or alternatively, the first locking feature may be an aperture and the locking member may further include a protrusion configured to slide into the first locking feature of the tubular member when the locking member is in the locked configuration. In addition or alternatively the first locking feature may be a penetrable material and the locking member may further include a protrusion configured to imbed into the penetrable material when the locking member is in the locked configuration. In addition or alternatively, the opening may include a narrower portion proximate a first end of the locking member and a wider portion proximate a second end of the locking member, the narrower portion configured to prevent the locking member from moving from the locked configuration to the unlocked configuration absent pressure applied to the second end of the locking member.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure.

What is claimed is:

1. A delivery device comprising:
    a needle having a proximal portion and a distal portion configured to be removeably positioned within a lumen defined by a dilator of a medical device assembly; and
    a handle having a proximal portion and a distal portion, the distal portion of the handle being fixedly coupled to the proximal portion of the needle, the distal portion of the handle configured to slideably receive at least a proximal portion of the dilator, the distal portion of the handle including a locking member, the locking member being configured to be placed in a locked configuration and an unlocked configuration, the locking member including a sliding member having a length greater than a width of the handle, the sliding member having a portion slidably disposed within the handle, the sliding member having a first end and a second end, the portion of the sliding member slidably disposed within the handle defining an opening and at least one protrusion,
    the proximal portion of the dilator configured to pass through the opening of the sliding member when the locking member is in the unlocked configuration, the at least one protrusion configured to engage a first locking feature on the proximal portion of the dilator to prevent the dilator from being removed from the handle when the locking member is in the locked configuration, wherein the first end protrudes from a first side of the handle when the locking member is in the unlocked configuration, and wherein the second end protrudes from a second side of the handle when the locking member is in the locked configuration, the width of the handle being defined by a distance between the first side of the handle and the second side of the handle.

2. The delivery device of claim 1, wherein the first end has a first visual appearance and the second end has a second visual appearance that differs from the first visual appearance.

3. The delivery device of claim 2, wherein the first visual appearance is green and the second visual appearance is red.

4. The delivery device of claim 1, wherein the sliding member is configured to slide from the unlocked configuration to the locked configuration in response to user pressure on the first end.

5. The delivery device of claim 1, wherein the sliding member is configured to slide from the locked configuration to the unlocked configuration in response to user pressure on the second end.

6. The delivery device of claim 1, wherein the at least one protrusion is configured to imbed at least partially into the proximal portion of the dilator when the locking member is in the locked configuration.

7. The delivery device of claim 1, wherein the at least one protrusion is configured to slide into an aperture defined by the proximal portion of the dilator when the locking member is moved from the unlocked configuration to the locked configuration.

8. The delivery device of claim 1, wherein the opening on the sliding member includes a narrower portion proximate the first end of the sliding member and a wider portion proximate the second end of the sliding member, the narrower portion configured to prevent, via a friction fit, the dilator from being removed and the wider portion configured to permit free axial movement of the dilator.

9. A medical assembly comprising:
an implant for placement in a body of a patient;
a dilator configured to be coupled to the implant and including a proximal portion and a distal portion, the proximal portion defining a first locking feature; and
a delivery device configured to deliver the implant and comprising:
  a needle having a proximal portion and a distal portion, the dilator configured to be positioned over the needle,
  a handle having a proximal portion and a distal portion, the distal portion of the handle being fixably coupled to the proximal portion of the needle, the distal portion of the handle defining an opening configured to receive the proximal portion of the dilator, and
  a locking member disposed at least partially in the distal portion of the handle, the locking member being configured to be placed in a locked configuration and an unlocked configuration, the locking member including a sliding member having a length greater than a width of the handle, the sliding member having a portion slidably disposed within the handle, the sliding member having a first end and a second end, the portion of the sliding member slidably disposed within the handle defining an opening and at least one protrusion, the proximal portion of the dilator configured to pass through the opening on the sliding member when the locking member is in the unlocked configuration, the at least one protrusion configured to engage the first locking feature of the dilator to prevent the dilator from being removed from the handle when the locking member is in the locked configuration.

10. The medical assembly of claim 9, wherein the first end protrudes from a first side of the handle when the locking member is in the unlocked configuration the second end protrudes from a second side of the handle when the locking member is in the locked configuration, the width of the handle being defined by a distance between the first side of the handle and the second side of the handle.

11. The medical assembly of claim 9, wherein the first end has a first visual appearance the second end has a second visual appearance that differs from the first visual appearance.

12. The medical assembly of claim 11, wherein the first visual appearance is green and the second visual appearance is red.

13. The medical assembly of claim 9, wherein the first locking feature is an aperture through a sidewall of the dilator.

14. The medical assembly of claim 9, wherein the first locking feature is an aperture through a sidewall of the dilator, and the at least one protrusion is configured to slide into the aperture of the dilator when the locking member is in the locked configuration.

15. The medical assembly of claim 9, wherein the first locking feature is a penetrable material the at least one protrusion is configured to imbed into the penetrable material when the locking member is in the locked configuration.

16. The medical assembly of claim 9, wherein the opening on the sliding member includes a narrower portion proximate the first end of the sliding member and a wider portion proximate the second end of the sliding member, the narrower portion configured to prevent the locking member from moving from the locked configuration to the unlocked configuration absent user pressure applied to the second end of the sliding member.

17. The medical assembly of claim 9, further comprising: a sleeve coupled to the dilator.

18. A method for treatment of a pelvic floor disorder in a patient's body, the method comprising:
ensuring a locking member of a delivery device is in an unlocked configuration, the locking member being in a distal end portion of a handle of the delivery device, the locking member including a sliding member having a length greater than a width of the handle, the sliding member having a portion slidably disposed within the distal end portion of the handle, the sliding member having a first end and a second end, the portion of the sliding member slidably disposed within the handle defining an opening and at least one protrusion, the unlocked configuration being indicated by the first end of the sliding member protruding from a first side of the handle the second end of the sliding member opposite the first end being substantially flush with a second side of the handle, the width of the handle being defined by a distance between the first side of the handle and the second side of the handle;

inserting a dilator of a medical device assembly over a needle fixedly coupled to the handle of the delivery device and through the opening defined by the sliding member, the medical device assembly including an implant;

moving the locking member from the unlocked configuration to a locked configuration, the locked configuration preventing the dilator from being removed from the handle by engaging the at least one protrusion with a first locking feature on a proximal portion of the dilator, the locked configuration being indicated by the second end protruding from the second side of the handle and the first end being substantially flush with the first side of the handle;

inserting the delivery device the dilator inside the patient's body;

disassociating the dilator from the delivery device once the delivery device reaches a target body location in a pelvic floor region by placing the locking member into the unlocked configuration; and fixing the implant at a first location within the pelvic floor region.

19. The method of claim 18, wherein the first end of the sliding member has a first visual appearance and the second end of the sliding member has a second visual appearance, the first visual appearance assisting in ensuring that the locking member is in the unlocked configuration and the second visual appearance assisting in ensuring that the locking member is in the locked configuration.

20. The method of claim 18, wherein the first locking feature is an aperture through a sidewall of the dilator, further comprising:

aligning the at least one protrusion with the aperture prior to ensuring the locking member is moved from the unlocked configuration to the locked configuration.

* * * * *